(12) United States Patent
Lvovich et al.

(10) Patent No.: US 6,577,112 B2
(45) Date of Patent: Jun. 10, 2003

(54) METHOD AND APPARATUS FOR ON-LINE MONITORING OF QUALITY AND/OR CONDITION OF HIGHLY RESISTIVE FLUIDS

(75) Inventors: Vadim F. Lvovich, Cleveland Heights, OH (US); Frederick P. Boyle, Kirtland, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/803,299

(22) Filed: Mar. 9, 2001

(65) Prior Publication Data

US 2002/0125899 A1 Sep. 12, 2002

(51) Int. Cl.⁷ ............................................... G01N 27/00
(52) U.S. Cl. ..................... 324/71.1; 73/53.05; 73/61.43
(58) Field of Search ............................ 73/53.05, 61.43, 73/61.58; 324/698, 664, 694, 71.1; 340/603; 205/777.5

(56) References Cited

U.S. PATENT DOCUMENTS

| | | | | |
|---|---|---|---|---|
| 5,164,319 | A | 11/1992 | Hafeman et al. | 435/291 |
| 5,331,287 | A | 7/1994 | Yamagishi et al. | 324/724 |
| 5,494,831 | A * | 2/1996 | Kindler | 205/777.5 |
| 5,518,590 | A | 5/1996 | Fang | 205/780.5 |
| 5,656,767 | A | 8/1997 | Garvey, III et al. | 73/61.44 |
| 5,824,889 | A | 10/1998 | Park et al. | 73/116 |
| 5,889,200 | A | 3/1999 | Centers et al. | 73/53.01 |
| 5,973,503 | A | 10/1999 | Kuipers et al. | 324/698 |
| 6,028,433 | A | 2/2000 | Cheiky-Zelina et al. | 324/663 |
| 6,217,745 | B1 | 4/2001 | Fang | 205/775 |

FOREIGN PATENT DOCUMENTS

EP 1 014 082 6/2000
JP 406082408 3/1994

OTHER PUBLICATIONS

Electrical Conductivity Method for Evaluation of Oxidative Degradation of Oil Lubricants; Lubrication Engineering, vol. 48, 7, 539–544; 1991, by Atsushi Sato and Takashi Oshika.
Development of an On–Board Type Oil Deterioration Sensor; SAE Technical Paper Series, Oct., 1993; Morishita, et. al.; pp 311–317.
Proceedings of the Symposium on Chemical Sensors; The Electrochemical Society, Inc., Proceedings vol. 87–9; Turner.
In–Situ Oil Condition Monitoring in Passenger Cars; Lubrication Engineering, vol. 50, 8, 605–611; Lee et al.
Development of an Automatic Engine Oil–Change Indicator System; SAE Technical Paper Series; Schwartz et al.; Feb. 23–27, 1987.

(List continued on next page.)

*Primary Examiner*—Christine K. Oda
(74) *Attorney, Agent, or Firm*—Teresan W. Gilbert; Michael F. Esposito; Samuel B. Laferty

(57) ABSTRACT

An apparatus and method for monitoring a highly electrically-resistive fluid. The method includes applying across the fluid an AC signal that includes at least two different AC electrical potentials, with at least one AC electrical potential having a non-zero DC offset, measuring the fluid's electrical response at each applied potential, and analyzing the fluid quality and/or condition using the applied AC signal and the corresponding measured electrical responses. The invention finds application in conjunction with the on-line (i.e., while in use) monitoring a highly resistive fluids such as, e.g., lubricants, natural and/or synthetic motor oils optionally including standard additives and/or adjuncts, combustion engine fuels, other hydrocarbon-based fluids used in transportation and industrial applications, and the like.

40 Claims, 22 Drawing Sheets

OTHER PUBLICATIONS

A Capacitive Oil Deterioration Sensor; Saloka et al. (No date).

Oil Maintenance Tester: A New Device to Detect the Degradation Level of Oils; Lubrication Engineering; Nov. 1986; Kato et al.

In Situ Electrochemical Sensor for Mearsurement in Nonconductive Liquids; J. Electrochemical Society, vol. 140, No. 3, Mar. 1993; Joseph et al.

The development of in situ electrochemical oil–condition sensors; Sensors and Actuators B, 17 (1994) 179–185; Wang et al.

In situ monitoring of high–temperature degraded engine oil condition with microsensors; Sensors and Actuators B, 20 (1994) 49–54; Lee et al.

The application of a.c. impedance technique for detecting glycol contamination in engine oil; Sensors and Actuators B 40 (1997) 193–197; Wang et al.

"Smart Sensing" of Oil Degradation and Oil Level Measurements in Gasoline Engines; SAE Technical Paper Series; Mar. 6–9, 2000; Basu et al.

Development of an On–Board Type Oil Deterioration Sensor; SAE Technical Paper Series; Oct. 18–21, 1993; Morishita et al.

Low Cost Oil Deterioration Sensor for On–Board Diagnostics; Park et al. pp 6–14; Aug. 1998.

* cited by examiner

METHOD AND APPARATUS FOR ON-LINE MONITORING OF QUALITY AND/OR CONDITION OF HIGHLY RESISTIVE FLUIDS

FIELD OF THE INVENTION

The present invention relates to the art of fluid monitoring and analysis. The invention finds application in conjunction with on-line (i.e., while in use) monitoring of highly electrically resistive fluids such as, e.g., lubricants, natural and/or synthetic motor oils, standard additives and/or adjuncts, combustion engine fuels, other hydrocarbon-based fluids used in transportation and industrial applications, and the like, and will be described with particular reference thereto. More specifically, the present invention relates to a method and apparatus for on-line analysis of a highly electrically resistive fluid's quality and/or condition using a fluid's electrical response, or change in a fluid's electrical response to an applied AC signal to determine, e.g., the amount or depletion of performance additives, contamination with unwanted liquids or solids, general degradation of the fluid due to chemical breakdown, or other changes in the fluid's condition or quality. However, the present invention is also amenable to other like applications.

It is understood as used herein, a highly electrically resistive fluid refers to a fluid that has bulk resistivity at 20° C. greater than about $10^3$ ohm-m, preferably greater than about $10^5$ ohm-m and more preferably greater than about $10^6$ ohm-m.

It is understood as used herein, "AC" is used to refer to a voltage, that is, an electrical potential, that has a non-zero frequency; "DC voltage offset" or "DC offset" is used to refer to the time average value of an "AC voltage"; and "AC signal" is used to refer to a combination of AC voltages with DC offsets.

BACKGROUND OF THE INVENTION

Highly electrically resistive fluids are a critical component for the proper operation of many devices and/or processes. For example: lubricants are needed for an internal combustion engine to efficiently provide power over a long service life; high quality fuel is needed for proper engine operation with minimal emissions; and metal working fluid is needed for rapid waste metal removal and maximum tool life. Optimum performance is achieved when the fluid in question is of proper quality for the application, that is, the fluid preferably includes an appropriate base fluid and proper performance additives, e.g., corrosion inhibitors, friction modifiers, dispersants, surfactants, detergents, and the like. During use or consumption, the condition of the fluid should remain within determined limits, that is, chemical and/or other changes to the fluid should be limited to ensure proper performance. Changes that can occur to a fluid during use are, e.g., oxidation of the base fluid, depletion of performance additives, build-up of contaminants from external sources and/or from breakdown of the fluid's chemical components, and the like.

Often, device owners and/or process operators depend on suppliers to provide proper quality fluids, and depend on regular fluid maintenance to maintain proper fluid condition. However, the foregoing is inherently limited and does not provide protection against accidental fluid substitution, or catastrophic fluid failure. In addition, regularly timed maintenance intervals can be wasteful if a fluid, with remaining useful life, is prematurely replaced or refreshed. Such premature maintenance, however, is often desirable rather than risk damage or excessive wear due to overly degraded fluids. In any event, owners and/or operators can minimize fluid maintenance costs without risking damage or excessive wear if fluid maintenance occurs only at the end (natural or otherwise) of the fluid's usefulness based on the monitored fluid condition. Hence, an on-line fluid monitoring method and apparatus is desired which achieves a substantially "real-time" determination of the fluid's initial quality and of the fluid's continuing condition during use.

Heretofore, achieving an appropriate fluid monitoring method and apparatus for many applications has been difficult due to one or more reasons. For example, typical transportation and industrial fluids are complex mixtures of base fluids and additives that, even without contaminants, do not lend themselves to easy analysis. Often, the fluids are used and/or consumed in a relatively harsh environment that is not suitable for some analytical equipment and methods. Additionally when implementing the method and/or apparatus, there are always cost constraints to consider, both initial and long term.

To satisfy the cost and environmental constraints associated with real-time on-line fluid quality and/or condition monitoring, methods that measure electrical properties of fluids offer significant advantage. For complex fluids, where multiple changes in fluid chemistry and composition can confound single-point electrical property measurements, multi-point techniques are used. Two conventional "multi-point" techniques that measure electrical properties of fluids are voltage-dependent electrochemical analysis and frequency-dependent Electro-Impedance Spectroscopy (EIS).

There are a variety of voltage based electrochemical fluid analysis techniques, e.g., voltammetric techniques such as cyclic voltammetry (CV), square wave voltammetry (SWV), linear scan voltammetry (LSV), differential pulse voltammetry (DPV), and normal pulse voltammetry (NPV), and time based techniques such as modified chronoamperometry (MCA). Generally, in each of these techniques, a fixed or slowly varying DC voltage is applied between either two or three electrodes of an electrochemical cell and measurements of the resulting current are plotted as a function of voltage and/or time. Voltage based electrochemical techniques provide information about low-resistivity fluids. However, these techniques are, in general, not suitable for highly resistive fluids. The extremely low current levels produced in highly resistive fluids make analysis difficult, and for many fluids, non-conductive fluid components can coat the electrodes, thereby inhibiting meaningful analysis. Off-line, voltage-based electrochemical analysis of highly resistive fluids can be conducted with high-cost, high-sensitivity electronics that solve the low-current-level problems, and can utilize chemical separation of fluid components before analysis to solve the electrode-coating problem. The off-line equipment and methods are, however, unsuited to an on-line environment with real-time analysis. On the other hand, U.S. Pat. No. 5,518,590 to Fang discloses a voltage-based on-line electrochemical method and apparatus for fluid analysis that uses a cell with a conductive electrolyte liquid or gel-like interphase surrounding the electrodes to overcome limitations associated with highly resistive fluid. The Fang technique, however, suffers from the limited robustness of the specialized electrochemical cell, and consequently the technique does not lend itself to broad application.

Conventional frequency-dependent EIS, when applied to highly-electrically-resistive fluids, has been limited to applying an AC voltage with zero DC offset voltage, between two electrodes immersed in the fluid to be monitored. The applied AC voltage and resulting current are used to determine the fluid' electrical impedance. By using a multitude of frequencies, for example two as disclosed in European Patent Application EP 1 014 082 A2, Bauer et al., filed December 1999, both the bulk impedance of the fluid and the electrochemical properties of the fluid at the surface of the electrodes can be studied. While EIS is relatively low cost and not affected by highly resistive fluids, conventional frequency-dependent EIS does not provide the level of detail regarding fluid quality and condition that voltage-dependent electrochemical techniques provide.

Accordingly, the present invention provides a new and improved highly-electrically-resistive-fluid monitoring apparatus and method that overcomes the above-referenced problems and others.

SUMMARY OF THE INVENTION

The present invention relates to a method of monitoring a highly electrically resistive fluid. The method includes the steps of applying an AC electrical potential across the fluid at a first frequency and a first DC offset such that a first electrical response results; measuring the resulting first electrical response; applying the AC electrical potential across the fluid at a second frequency for a non-zero first DC offset voltage, and/or a second DC offset such that a second electrical response results, the second frequency and the second DC offset being different from the first frequency and the first DC offset respectively; measuring the resulting second electrical response; and analyzing the fluid's quality and/or condition from the measured first and second electrical responses to the respective first and second applied electrical potentials.

The method can further include repeatedly applying the AC potentials, repeatedly measuring the resulting electrical responses, and analyzing the quality and/or condition of the fluid using the measured first and second electrical responses and/or changes in the measured first and second electrical responses to the respective first and second applied electrical potentials.

The method can further include the step of controlling the applied AC potentials based on determined electrical impedance, analyzed fluid quality and/or condition if the AC potentials are repeatedly applied.

The method can further include measuring the fluid's temperature.

The method can further include compensating the fluid quality and/or condition analysis for variations in fluid temperature.

The method can further include the step of heating the fluid to a desired temperature.

The method can further include the step of controlling the applied AC potentials based on measured temperature.

The method can further include the step of determining the quality of a refreshment fluid when either a complete replacement or a partial refreshment of the monitored fluid occurs.

In another aspect of the invention, the first and second electrical responses are currents resulting from the applied AC electrical potentials.

In another aspect of the invention, the fluid quality and/or condition can be analyzed using electrical impedance values determined from measured electrical responses corresponding to applied electrical potentials.

In another embodiment of the invention, the method includes the steps of applying across the highly electrically-resistive fluid an AC signal that includes at least two different AC electrical potentials with at least one AC electrical potential having a non-zero DC offset, measuring the fluid's electrical response at each applied potential, and analyzing the quality and/or condition of the fluid using the applied AC signal and corresponding measured electrical responses.

The method can further include repeatedly applying the AC signal, repeatedly measuring the resulting electrical responses, and analyzing the quality and/or condition of the fluid using the applied AC signal and measured and/or changes in the measured corresponding electrical responses.

In another aspect of the invention, the AC signal can be AC electrical potentials where DC offset is held fixed and frequency is effectively swept from one frequency to another either in a continuous manner or in a series of discreet frequency steps for at least one non-zero DC offset.

In another aspect of the invention, the AC signal can be AC electrical potentials where frequency is held fixed and DC offset voltage is effectively swept from one DC offset voltage to another either in a continuous manner or in a series of discreet voltage steps for at least one frequency.

In accordance with another aspect, the present invention further includes a highly-electrically-resistive-fluid monitoring apparatus having at least a pair of separated electrodes that are immersed in a fluid being monitored; at least one signal generator that applies to the electrodes an electrical signal with at least two different AC potentials with at least one potential having a non-zero DC offset; at least one monitor that measures an electrical response to the applied signal; and a controller that analyzes applied electrical signal and corresponding measured electrical responses to determine the quality and/or condition of the fluid.

In another aspect of the invention the monitor(s) is a current sensor, which measures a current generated in response to the applied potentials.

In another aspect of the invention, the controller that analyzes the quality and/or condition of the fluid can control the signal generator.

In another aspect of the invention, the apparatus can further include a temperature sensor that monitors a temperature of the fluid.

In another aspect of the invention, the apparatus can further include means for compensating the fluid quality and/or condition analysis for variations in fluid temperature.

In another aspect of the invention, the apparatus can further include temperature control means for regulating the temperature of the fluid.

In another aspect of the invention, the apparatus can further includes means for controlling the signal generator(s) based on the monitored temperature of the fluid.

In another aspect of the invention, the apparatus can further include means for determining when the fluid being monitored is totally replaced.

In another aspect of the invention, the apparatus can further include means for determining when the fluid being monitored is partially refreshed and the concentration of the refreshment fluid.

In another aspect of the present invention, the apparatus for monitoring highly electrically-resistive fluids includes sensing means in contact with a fluid being monitored. Further included are signal generating means in electrical communication with the sensing means. The signal generating means apply to the sensing means electrical signal having AC potentials of selected frequencies and selected DC offsets. The frequencies are selected such that there are at least two different frequencies for a non-zero DC offset, and/or the DC offsets are selected such that there are at least two different DC offsets. Monitoring means measure electrical response to the electrical signal via the sensing means. Control means analyzes the quality and/or condition of the fluid using the applied electrical signals and corresponding measured electrical responses.

One advantage of the present invention is that both the AC and DC dependence of a highly electrically-resistive fluid's electrochemical properties are analyzed.

Another advantage of the present invention is that the time required to determine the electrochemical detail can be optionally reduced by fluid heating.

Another advantage of the present invention is that the temperature dependant nature of the electrochemical measurements can be optionally compensated.

Another feature of the present invention is that the applied electrical signal can be optionally controlled based on the analyzed fluid quality, or fluid condition, and/or the monitored fluid temperature.

Another advantage of the present invention is that refreshment of the monitored fluid can be determined to allow analysis of the refreshment fluid's quality.

Another advantage of the present invention is that the fluid analysis provided can include an analysis of a highly electrically-resistive fluid's solution, bulk, charge transfer, electrochemical reaction properties and the like.

Another advantage of the present invention is its compatibility with on-line environments.

Still further advantages, features and benefits of the present invention will become apparent to those of ordinary skill in the art upon reading and understanding the following detailed description of the preferred embodiments.

DETAILED DESCRIPTION OF THE PREFERRED EMBODIMENT(S)

Figure 1:
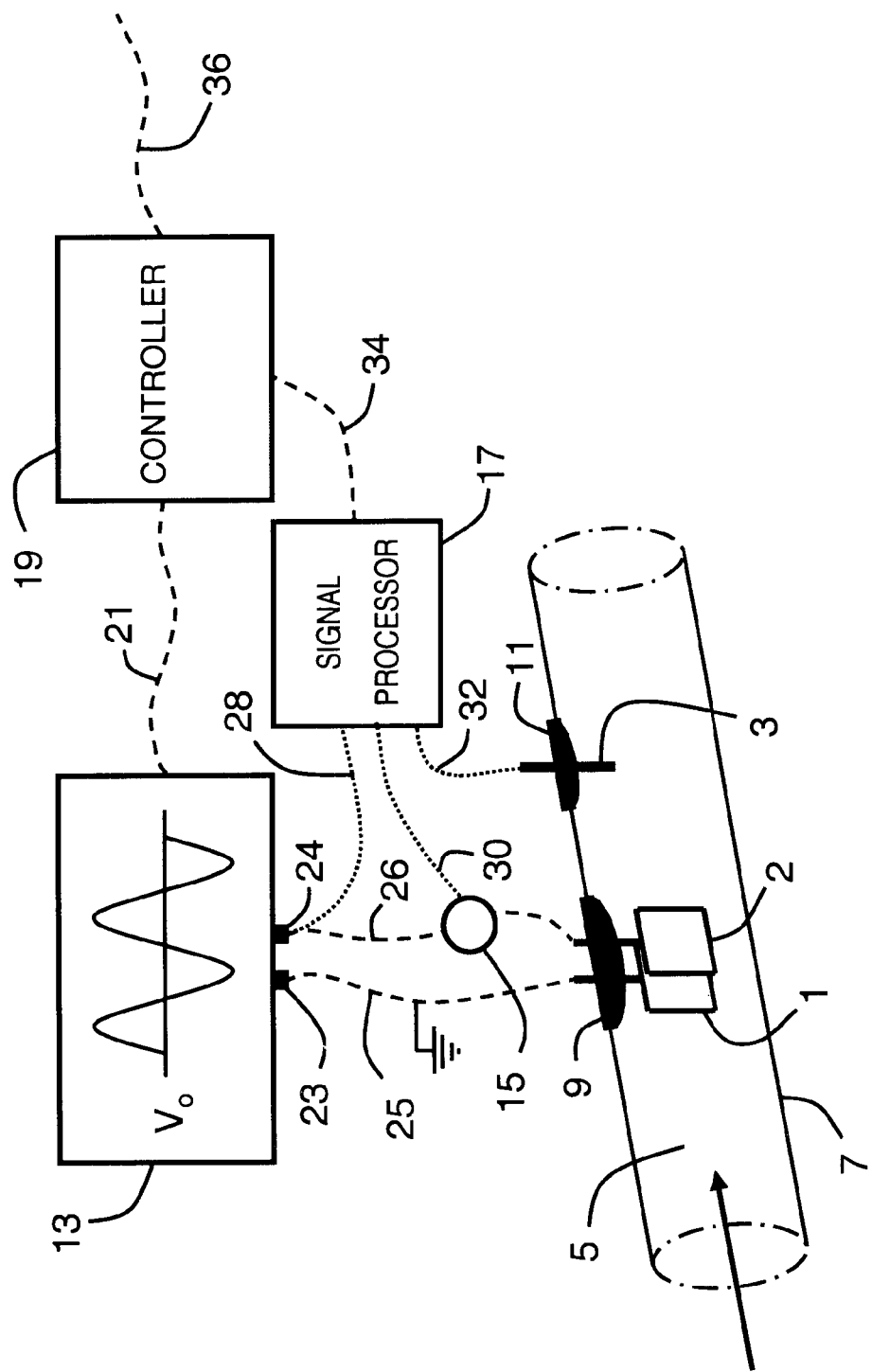
FIG. 1 is a schematic illustration showing an on-line fluid monitoring apparatus in accordance with aspects of the present invention.

With reference to FIG. 1, an on-line fluid monitoring device or apparatus is shown. As illustrated, the on-line fluid monitoring device includes having a pair of separated electrodes 1 and 2, and a thermocouple 3, or other temperature sensing device, which are both immersed in a fluid 5 flowing or otherwise present in conduit 7. Fluid 5 in this embodiment, and in all the embodiments described herein, is a highly-electrically resistive fluid such as, e.g., a lubricant, a natural and/or synthetic motor oil optionally including standard additives and/or adjuncts, a combustion engine fuel, a hydrocarbon-based fluid used in transportation and industrial applications, and the like. Electrodes 1 and 2 can be constructed of the same material or can be constructed of different materials. The materials are selected from the group consisting of any conductive material, preferably a metal such as stainless steel, platinum, copper, nickel, aluminum and the like. In a preferred embodiment, electrodes 1, 2 are fixedly held in and electrically isolated from conduit 7 by mount 9. Likewise, thermocouple 3 is fixedly held in conduit 7 with mount 11.

The fluid monitoring apparatus also preferably includes a multi-frequency, multi-offset-voltage signal generator 13, a current sensor 15, a signal processor 17 and a controller 19. Through an electrical conduit 21, controller 19 controls the frequency and DC offset of AC potentials supplied by signal generator 13 to outputs 23, 24. The signal generator 13 via outputs 23, 24, applies an electrical potential to electrodes 1, 2 using electrical conduits 25, 26, respectively. That is, signal generator 13 applies an electrical potential across electrodes 1, 2, wherein the electrical potential includes a selected AC component and a selected DC offset voltage. Optionally, as shown, electrical conduit 25 is grounded to provide a voltage reference.

Current sensor 15 measures electrical current flow resulting from the applied electrical signal and is connected, preferably, to electrical conduit 26 as shown. Signal processor 17 monitors signal generator 13 through electrical conduit 28, current sensor 15 through electrical conduit 30 and thermocouple 3 through electrical conduit 32. Signal processor 17 converts the monitored inputs into suitable signals that are input to controller 19 through electrical conduit 34. Controller 19 in turn uses the signals from signal processor 17 to analyze a condition and/or quality of fluid 5 in conduit 7. Controller 19 can then communicate information about the analyzed condition and/or quality of fluid 5 through communication conduit 36.

In operation, controller 19 is programmed to command signal generator 13 to output AC voltages at a plurality of determined frequencies and DC offset voltages. For example, controller 19 is preferably programmed to command signal generator 13 to output AC voltages with a zero DC offset voltage while effectively sweeping from one frequency to a second frequency at a determined rate, followed by a second frequency sweep with a first non-zero DC offset voltage, followed by a third frequency sweep at a second non-zero DC offset voltage different from the first non-zero DC offset voltage, and so on with the sequence being repeated after a desired number of DC offset voltages. In another embodiment, controller 19 is optionally programmed to command signal generator 13 to output an AC voltage at a first fixed frequency as DC offset voltages are effectively swept between zero volts and a determined maximum voltage, followed by a second DC offset voltage sweep at a second fixed frequency different than the first frequency, followed by a third DC offset voltage sweep at yet another third fixed frequency, and so on with the sequence ultimately repeating itself after a desired number of frequencies depending on characteristic properties of fluids and degradation modes of fluid. In still another embodiment, controller 19 is optionally programmed to command signal generator 13 to output an AC voltage at a first fixed frequency/DC-offset-voltage for a determined number of cycles, followed by a different second fixed frequency/DC-offset-voltage, etc. until a complete sequence of discrete frequency/DC-offset-voltages is completed, and then repeating the sequence. Optionally, controller 19 is programmed to command signal generator 13 to output an appropriate electrical signal based on the analysis of the inputs from signal processor 17. In any event, for each data set, the applied signal is selected such that at least two different frequencies are included for a non-zero DC offset, and/or at least two different DC offset voltages are included.

In a preferred embodiment, as signal generator 13 applies the designated signal to electrodes 1, 2, signal processor 17 monitors: the applied electrical potentials across electrodes 1, 2 via electrical conduit 28; the resulting or associated currents using current sensor 15 and electrical conduit 30; and the temperature of fluid 5 using thermocouple 3 and electrical conduit 32. Signal processor 17 compares the magnitude and phase of monitored voltages and currents to calculate or otherwise determine the electrochemical impedance of fluid 5.

The frequency range used to monitor and analyze the fluid is in the range of about 1 millihertz (mHz) to about 100 megahertz (MHz), preferably about 1 mHz to about 10 MHz, and more preferably about 10 mHz to about 10 MHz.

The DC offset voltage is in the range of about −40V to about 40 V, preferably about −30V to about 30V, and more preferably about −15V to about 15V. Switching polarity of the applied DC offset to the electrodes is not necessary if the electrodes 1, 2 are constructed of the same material. However, if the electrodes are constructed with different materials, the switching polarity of the DC offset voltage may be helpful in determining the fluid's electrochemical detail.

The AC peak amplitude is in the range of greater than 0V to less than or equal to about 10V, preferably about 0V to about 3V and more preferably about 0V to about 1.5V.

The rate is determined by taking data for at least one complete cycle for each tested frequency. Generally a sweep from about 10 MHz to about 10 MHz, using about 116 frequencies, taking data for two cycles at each frequency, occurs in about 50 minutes.

Figure 2:
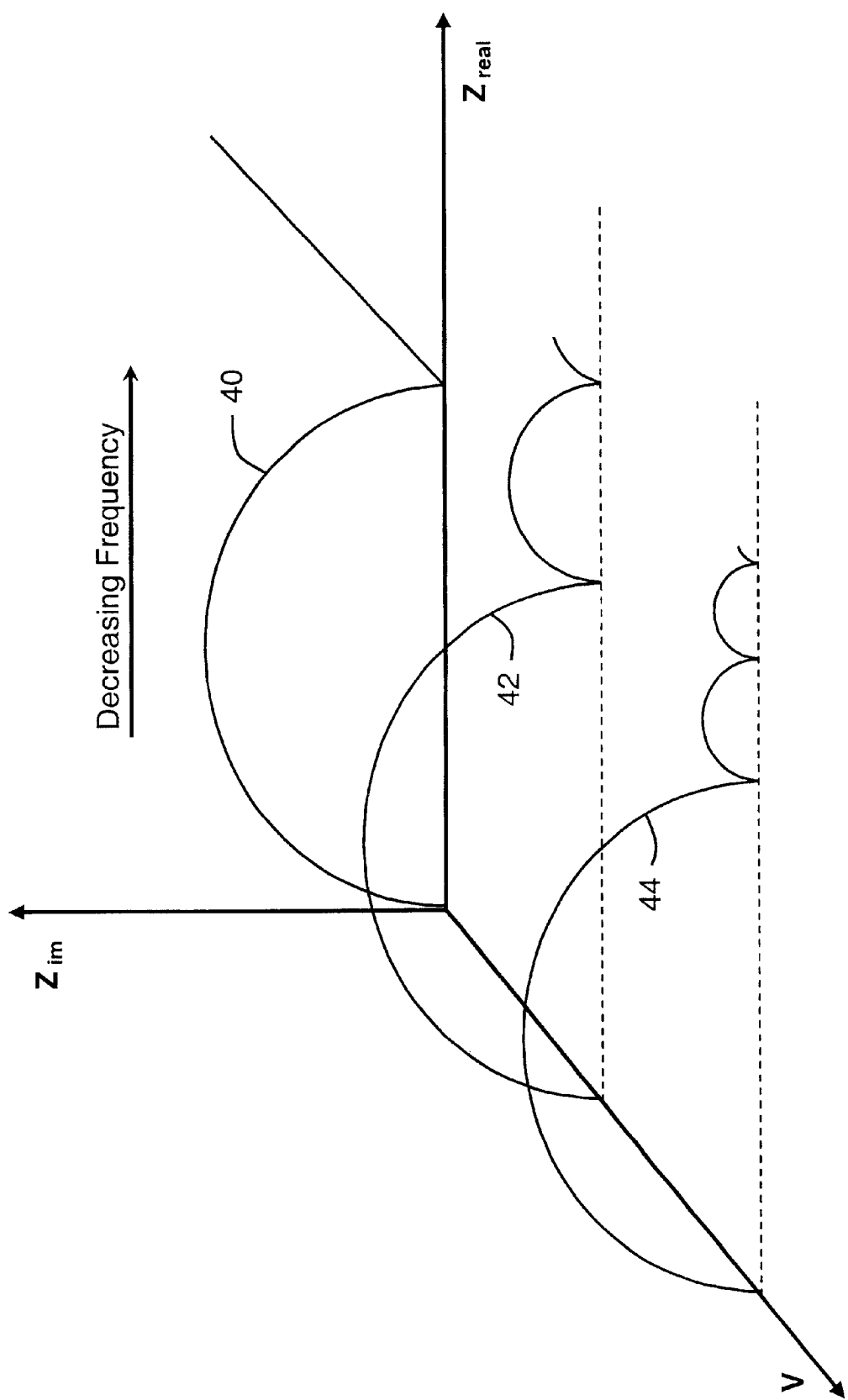
FIG. 2 is a representative graph illustrating the electrochemical impedance of a fresh highly electrically-resistive fluid.

FIG. 2 shows a graph of electrochemical impedance, known as Nyquist plots, which are representative of data obtained in accordance with aspects of the present invention. FIG. 2 shows a graph consistent with a fresh, highly electrically-resistive fluid 5. As shown in FIG. 2, a complete sequence of swept frequencies for zero and two different non-zero DC offset voltages were obtained. Referring to FIG. 2, at DC offset voltage V, fluid 5 has an imaginary impedance $Z_{im}$ and real impedance $Z_{real}$ associated with each frequency. The frequency dependent $Z_{im}$ and $Z_{real}$ are plotted against one another to obtain the Nyquist plot for that DC offset voltage. Optionally, instead of swept frequencies, the graph can contain only individual data points for discretely applied frequencies, or may be an appropriate curve fit to individual data.

Referring again to FIG. 1, using electrical conduit 34, signal processor 17 preferably communicates to controller 19 calculated impedance values (imaginary and real) for each signal applied, or alternately equivalent information related thereto, along with temperature information from thermocouple 3. Controller 19 uses the information from signal processor 17 as inputs to analyze, preferably by an algorithm, the quality and/or condition of fluid 5. The temperature information is advantageous for fluid condition and quality analysis insomuch as the electrochemical properties of fluids can be temperature dependent. Preferably, controller 19 or signal processor 17 uses the temperature information to normalize measurements to a determined standard temperature, which is typically the normal operating temperature of the fluid, or otherwise compensate for variations in fluid temperature from measurement to measurement. Without the temperature information, changes in temperature of fluid 5 could be misinterpreted as changes in fluid's condition.

Controller 19 analyzes the quality and/or condition of fluid 5 either from information obtained during the sequence of applied electrical potentials, or from changes in information between sequences of the applied electrical potentials. To illustrate, by way of example, how data from signal processor 17 contains fluid quality and condition information, graphs of electrochemical impedance of a fresh fluid and the same fluid in two different states of deterioration are described and compared.

In FIG. 2, curve 40 is a plot of $Z_{real}$ and $Z_{im}$ for a swept frequency range with a zero DC offset voltage. This is the curve that is produced by a conventional frequency-dependent EIS technique. The very first portion of curve 40, which is a short, essentially linear, region with near zero $Z_{im}$ measured at very high frequencies, is associated with solution resistance properties of fluid 5. The semi-circular portion of curve 40, measured at mid-range frequencies, is associated with bulk properties of fluid 5; and the rising tail portion of curve 40, measured at lower frequencies, is associated with charge transfer properties of fluid 5. Note that curve 40 contains relatively little information about the detailed nature of the fluid's charge transfer properties and no information about electrochemical reactions that might occur at electrodes 1, 2. On the other hand, curves 42 and 44 show the electrochemical impedance of the fluid for the same AC frequency range as curve 40, but with two different non-zero DC offset voltages as per the invention. The additional features (i.e., the smaller semi-circular regions) contained in curves 42 and 44 at lower frequencies provide additional information about the fluid's charge transfer and electrochemical reaction properties. Consequently, this additional information is useful in analyzing the fluid's composition or formulation. That is, for a fresh highly electrically-resistive fluid, with appropriate selection of DC offset voltages and AC frequencies for the applied signals, a study or appropriate analysis of the electrochemical impedance may be undertaken to determine whether the fluid is of proper quality for the intended application.

Figure 3:
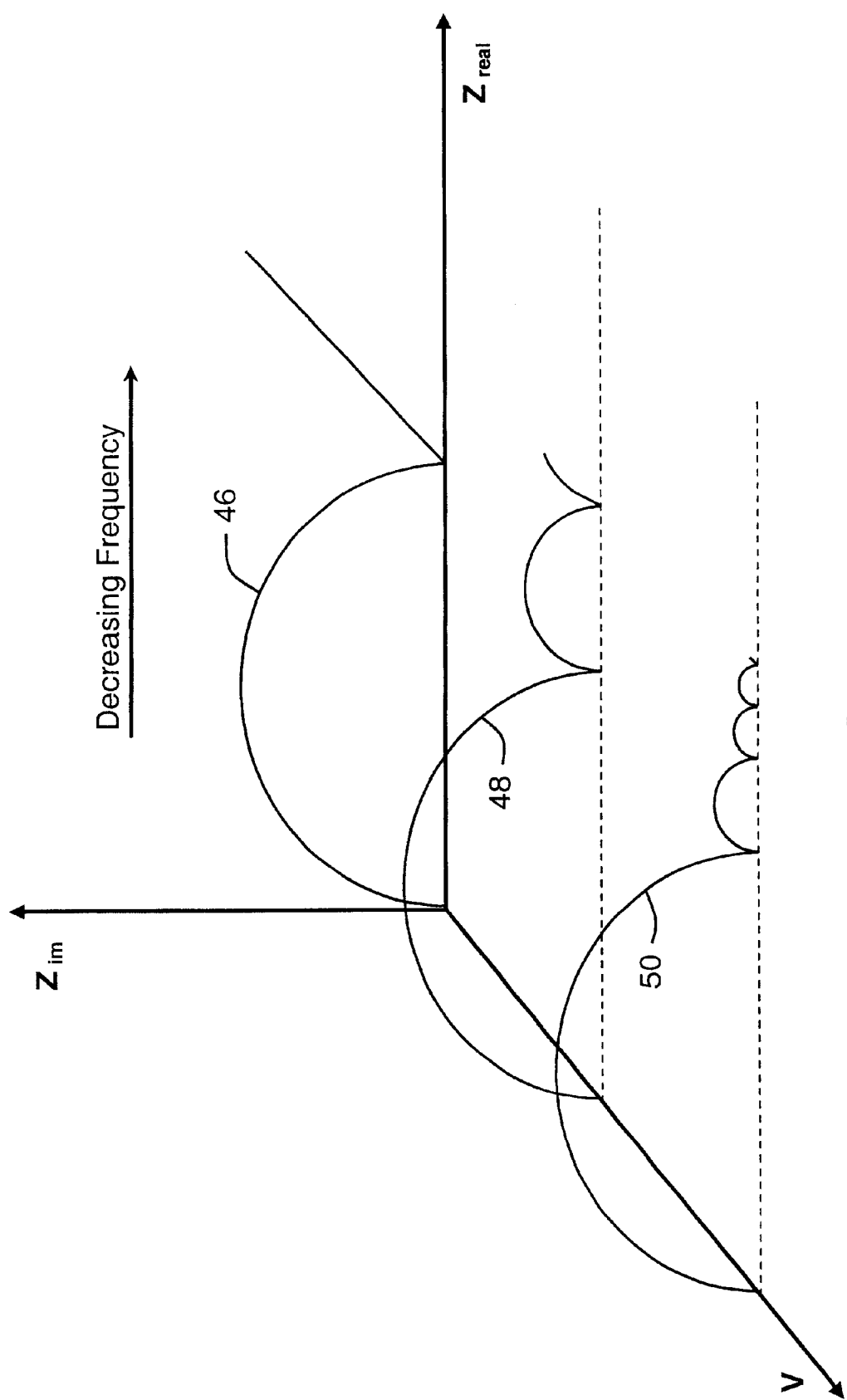
FIG. 3 is a representative graph illustrating the electrochemical impedance of the fluid of FIG. 2 after being deteriorated due to oxidation.

FIG. 3 shows the same fluid of FIG. 2 with the difference being that in FIG. 3 the fluid has undergone deterioration due to oxidation. With additional reference to FIG. 3, curves 46, 48 and 50 correspond to the same frequency range and DC offset voltages as curves 40, 42 and 44, respectively, of FIG. 2. Comparing the curves of the two figures, zero DC offset voltage curve 46 and first non-zero DC offset voltage curve 48 have only minor differences from curves 40 and 42. However, at the higher DC offset voltage, curve 50 has significant differences from curve 44. In particular, curve 50 shows a change in number and relative magnitude of individual semi-circular shaped regions, when compared to curve 44, which can be analyzed to determine that the fluid's condition has changed due to oxidation.

Figure 4:
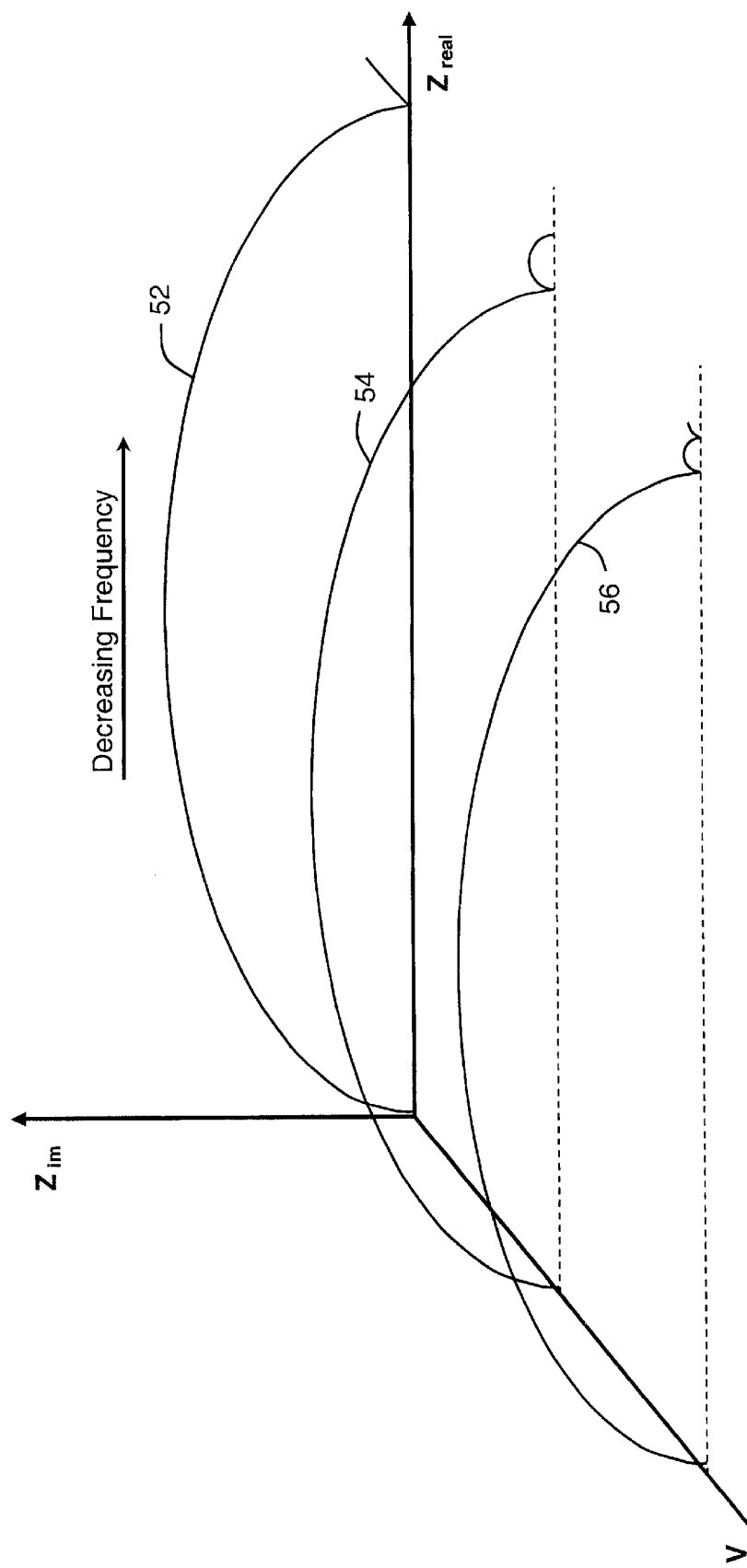
FIG. 4 is a representative graph illustrating the electrochemical impedance of the fluid of FIG. 2 after being deteriorated due to contamination.

FIG. 4 shows the same fluid of FIG. 2 with the difference being that in FIG. 4 the fluid has undergone deterioration due to contamination. With additional reference to FIG. 4, curves 52, 54 and 56 correspond to the same frequency range and DC offset voltages as curves 40, 42 and 44, respectively, of FIG. 2. Comparing the curves of FIG. 4 and FIG. 2, the contamination causes significant change in features for each DC offset voltage. In particular, the size and shape of region associated with the fluid bulk properties in all three curves 52, 54, 56 shows that a major fluid condition change has occurred.

With particular attention again to FIG. 1, controller 19 analyzes, using an appropriate algorithm, the quality and/or condition of fluid 5 based upon input from signal processor 17 and communicates designated information as desired to external components or systems through communication conduit 36. The communicated information, for example, is used to power or trigger a signaling device (not shown) that alerts an operator or service technician when the fluid is not of the proper quality or is out of a desired condition range. Alternately, the communicated information passed along conduit 36 is used by a higher level system (not shown) that maintains the condition of fluid 5 or that controls a device using fluid 5. In addition to using input from signal processor 17 to analyze fluid quality and/or condition, when optionally programmed, controller 19 also uses the signal processor input to regulate the commanded AC voltage frequencies and DC offsets of signal generator 13 in order to optimize the monitoring and analysis of the quality and/or condition of fluid 5.

While the embodiment shown in FIG. 1 has separate modules for the signal generator, the electrodes, the current sensor, the signal processor, the controller, and other elements, any two or more of the functions carried out thereby are, optionally, incorporated into a combined module to achieve desired efficiencies in cost, data processing, design or the like. Likewise, the combining of elements or modules is also contemplated where appropriate in other embodiments described herein.

Figure 5:
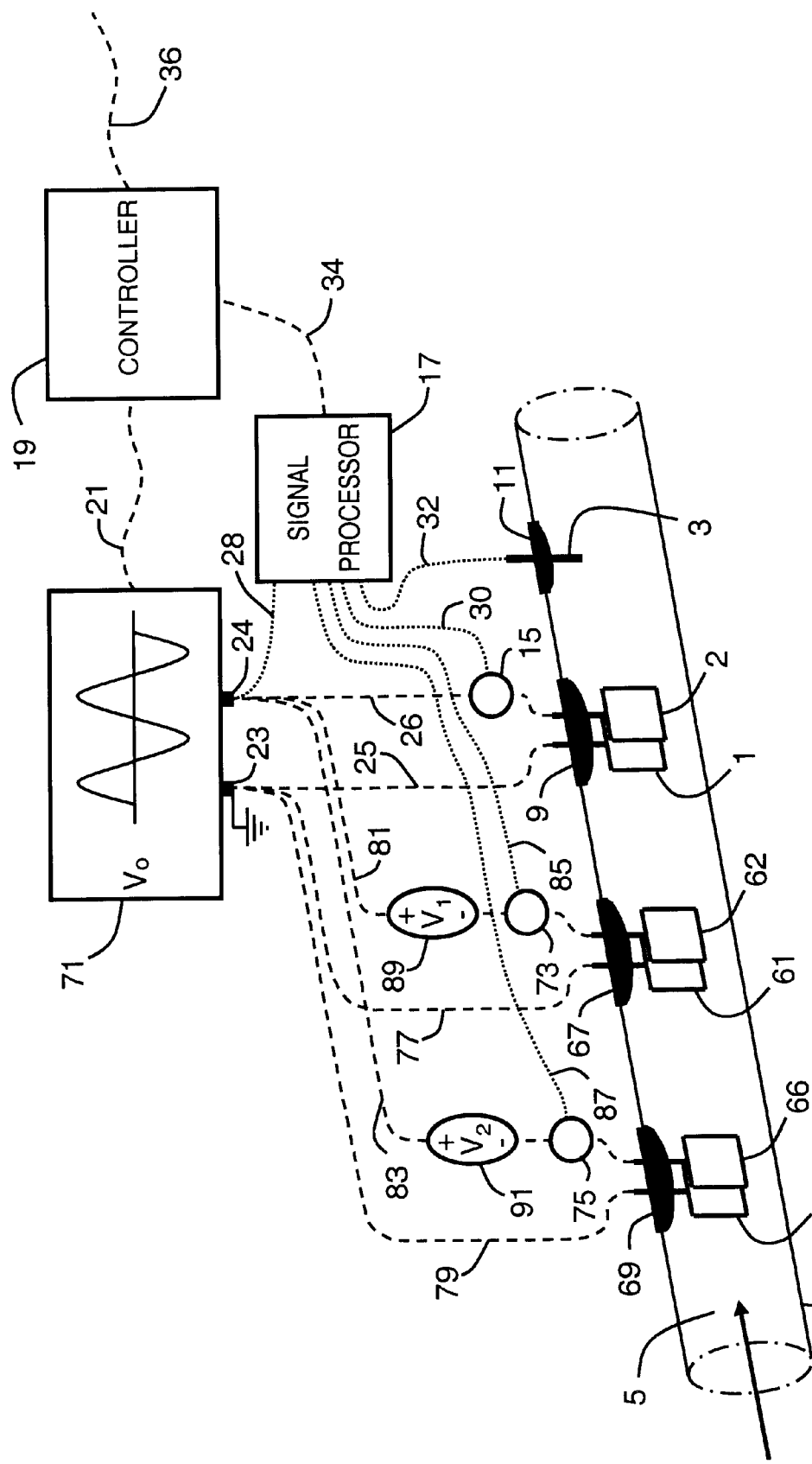
FIG. 5 is a schematic illustration showing another embodiment of an on-line fluid monitoring apparatus in accordance with aspects of the present invention.

With reference to FIG. 5, another embodiment of the on-line fluid monitoring apparatus is shown which provides, consistent with real-time monitoring, a more rapid measurement/analysis (as compared to the embodiment of FIG. 1) of fluid 5 in conduit 7. The time saving is realized by employing multiple electrode pairs in parallel to simultaneously measure the electrochemical properties of fluid 5 at differing DC offset voltages. More specifically, as shown in FIG. 5, there are three 5, electrode pairs 1 & 2, 61 & 62 and 65 & 66, respectively, immersed in fluids that are fixedly held in and electrically isolated from conduit 7 by mounts 9, 67 and 69, respectively. While three electrode pairs are shown for exemplary purposed herein, a greater or lesser number of electrode pairs may be similarly employed as desired.

A thermocouple 3 or other temperature sensor is also fixedly held in conduit 7 with mount 11 such that the temperature of fluid 5 is monitored. The fluid-monitoring apparatus of FIG. 5 also includes a multi-frequency, zero-DC offset, signal generator 71, current sensors 15, 73, 75, a signal processor 17 and a controller 19. Through electrical conduit 21, controller 19 controls the frequency supplied by signal generator 71 to outputs 23, 24. Output 23 is shown as grounded to provide a voltage reference, and is connected to electrodes 1, 61, 65 through electrical conduits 25, 77, 79 respectively. Electrical conduit 26 electrically connects output 24 to electrode 2 and includes current sensor 15. Electrical conduits 81, 83 electrically connect output 24 to electrodes 62, 66 respectively and include current sensors 73, 75 and electrical elements 89, 83 respectively. Electrical elements 89, 83 provide fixed DC offset voltages $V_1$, $V_2$ respectively to the AC voltage from signal generator 71. For example, electrical elements 89, 83 are optionally batteries with fixed DC output voltages $V_1$, $V_2$.

Signal processor 17 monitors: the applied voltage of signal generator 71 through electrical conduit 28; the resulting current using current sensors 15, 73, 75 and electrical conduits 30, 85, 87, respectively; and the temperature of fluid 5 using thermocouple 3 and electrical conduit 32. Signal processor 17 converts the monitored inputs into suitable signals that are input to controller 19 through electrical conduit 34. Controller 19 uses signals from signal processor 17 to analyze the condition and/or quality of fluid 5 in conduit 7. Controller 19 communicates information about the condition and/or quality of fluid 5 through communication conduit 36.

In operation, the components in FIG. 5 function similarly to their counterparts in FIG. 1. In particular, controller 19 is programmed to command signal generator 71 to output AC voltages at a multitude of determined frequencies. For example, controller 19 is optionally programmed to command signal generator 71 to repeatedly sweep from one frequency to a second frequency at a determined rate. In another example, controller 19 is optionally programmed to command signal generator 71 to output an AC voltage at one fixed frequency for a determined number of cycles, followed by a second different fixed frequency, etc. until a complete sequence of discrete frequencies is completed, and then the sequence is repeated. In another example, controller 19 is optionally programmed to command signal generator 71 to output AC voltages based on inputs from signal processor 17.

For each AC voltage generated by signal generator 71; using electrical conduits 25, 26, electrode pair 1, 2 applies the generated AC voltage to fluid 5 with zero DC offset voltage; using electrical conduits 77, 81 and electrical element 89, electrode pair 61, 62 applies the generated AC voltage to fluid 5 with a DC offset voltage of $V_1$; and using electrical conduits 79, 83 and electrical element 91, electrode pair 65, 66 applies the generated AC voltage to fluid 5 with a DC offset voltage of $V_2$. In this manner, signal generator 71 is relieved from providing multiple DC offset voltages insomuch as they are provided by electrical elements 89, 91.

In similar fashion to the embodiment of FIG. 1, as the signal is applied to fluid 5, signal processor 17 monitors: the output of signal generator 71 through electrical conduit 28; the currents from current sensors 15, 73, 75 through electrical conduits 30, 85, 87, respectively; and the temperature of fluid 5 using thermocouple 3 and electrical conduit 32. As shown in FIG. 5, signal processor 17 optionally uses only one input from signal generator 71 to monitor the signal being applied to electrode pair 1, 2, and the known electrical characteristics of electrical elements 89, 91, are used to calculate the composite signal being applied to electrode pairs 61, 62 and 65, 66, respectively. Alternately, signal processor 17 directly monitors the signal being applied to electrode pairs 61, 62 and 65, 66 by having additional electrical conduits (not shown) attached to electrical conduits 81 and 83 between electrical elements 89 and 91 and electrodes 62, 66, respectively. As before, signal processor 17 compares the magnitude and phase of measured or calculated applied voltages and measured currents to calculate the electrochemical impedance of fluid 5. As in the embodiment shown in FIG. 1, signal processor 17 communicates the calculated or otherwise determined electrochemical impedance and temperature information to controller 19 through electrical conduit 34 where, with the use of an appropriate algorithm, controller 19 continuously analyzes the quality and/or condition of fluid 5, and, when so programmed, alters the commanded frequencies to be output by signal generator 71. As in the embodiment of FIG. 1, fluid 5 quality and condition information communicated by controller 19 is optionally used, for examples, to power or trigger a signaling device (not shown) that alerts an operator or service technician when the fluid is not of the proper quality or is out of a desired condition range. Optionally, the information communicated via conduit 36 is used by a higher level system (not shown) that maintains the condition of fluid 5 or that controls a device using fluid 5.

The device of FIG. 5 supplies the different DC offset voltages via multiple electrode pairs and electrical elements 89 and 91 instead of supplying the different DC offset voltages via the signal generator. In this manner, a plurality of frequency sweeps at differing DC offset voltages are obtainable simultaneously with the FIG. 5 apparatus, thereby reducing the measurement sequence and/or data collection time relative to the FIG. 1 apparatus. In other respects, the two embodiments are substantially similar.

Figure 6:
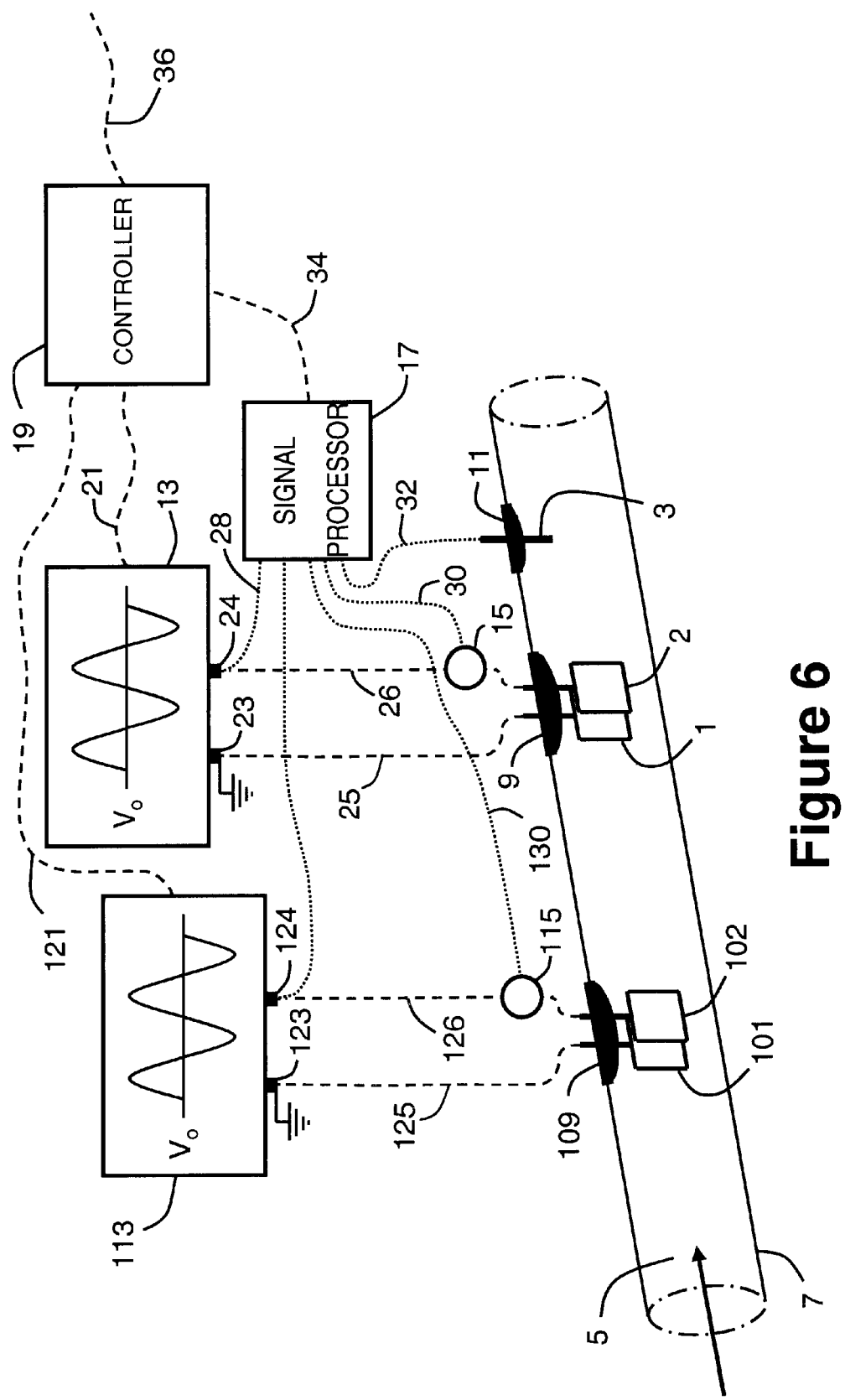
FIG. 6 is a schematic illustration showing another embodiment of an on-line fluid monitoring apparatus in accordance with aspects of the present invention.
Figure 7A:
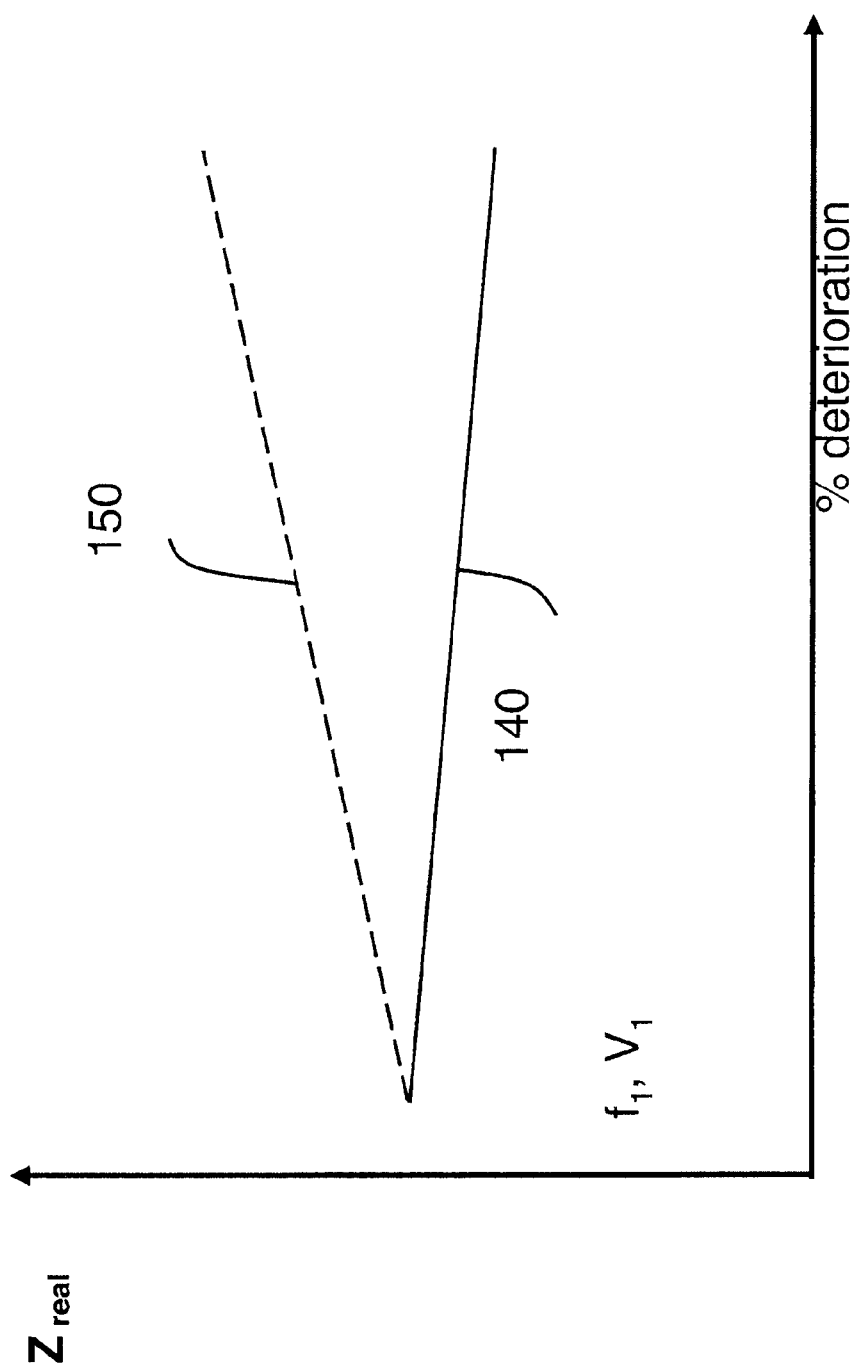
FIGS. 7(A)-7(F) include representative graphs illustrating the oxidation and contamination deterioration dependence of a highly electrically-resistive fluid's electrochemical impedance monitored at three fixed frequencies and offset voltages.
Figure 7B:
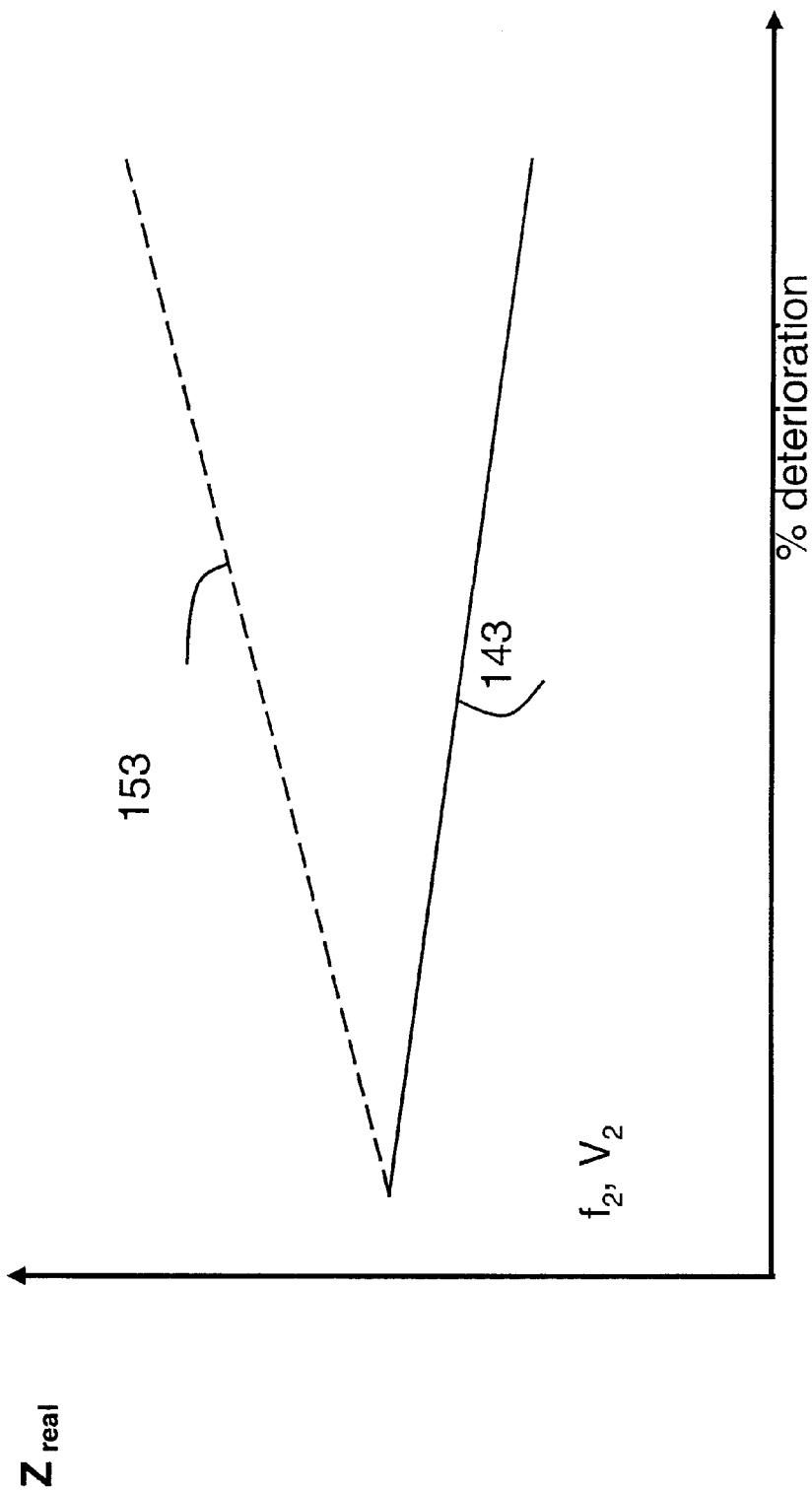
Figure 7C:
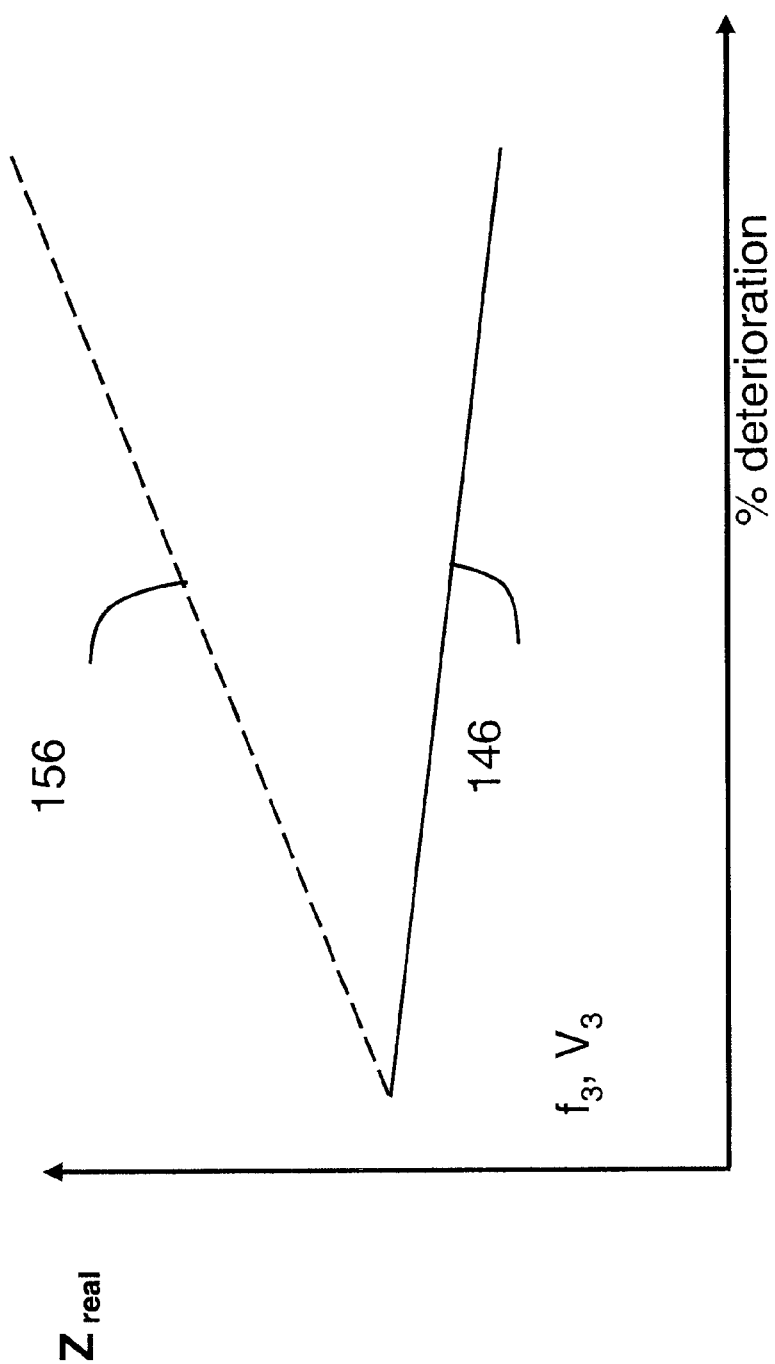
Figure 7D:
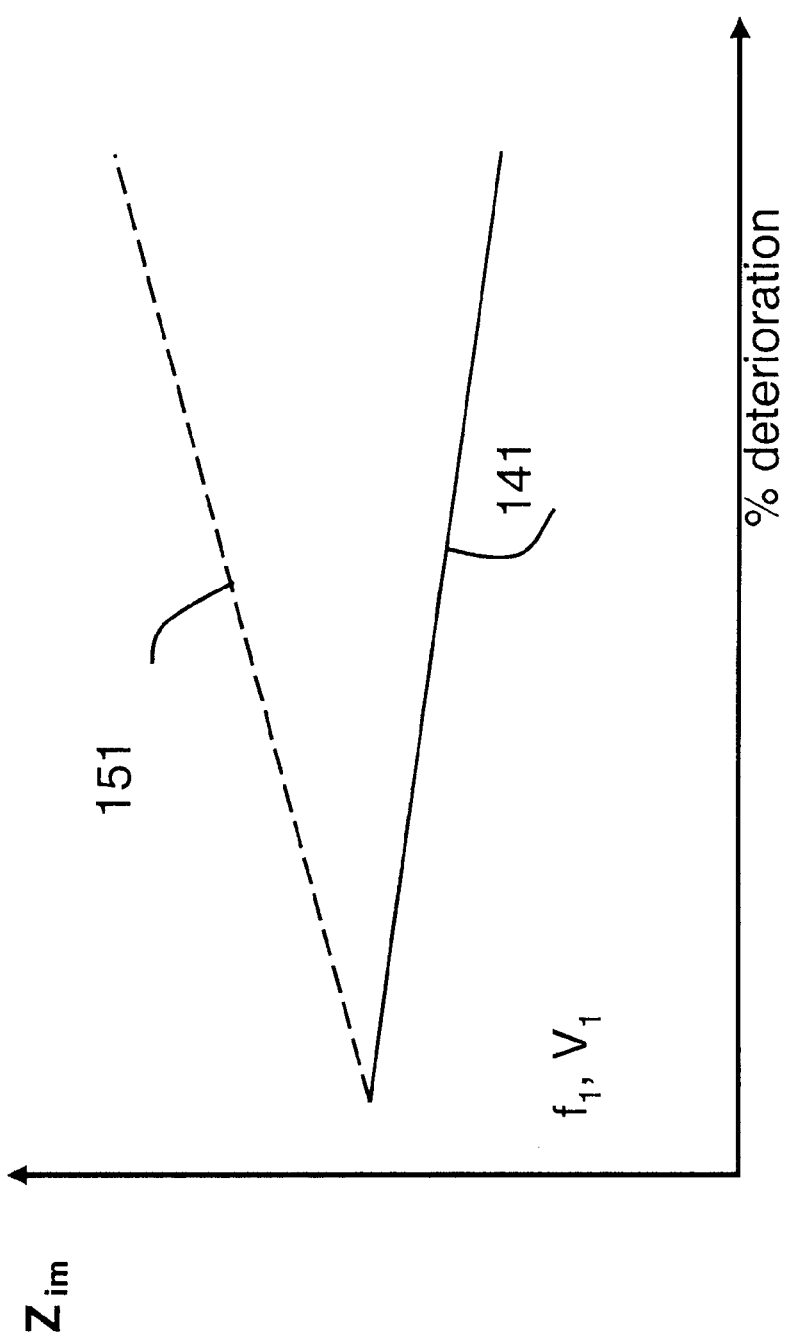
Figure 7E:
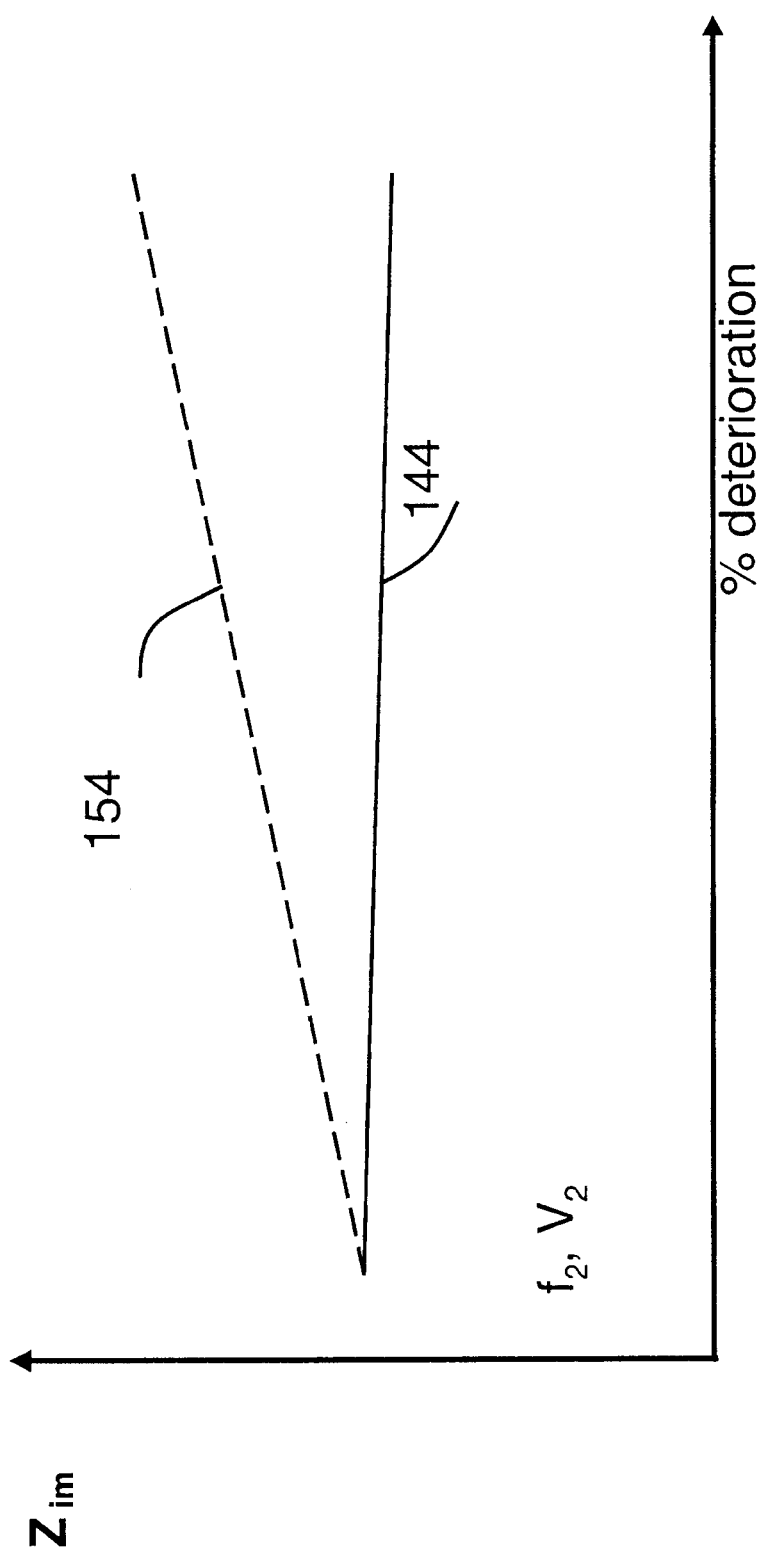
Figure 7:
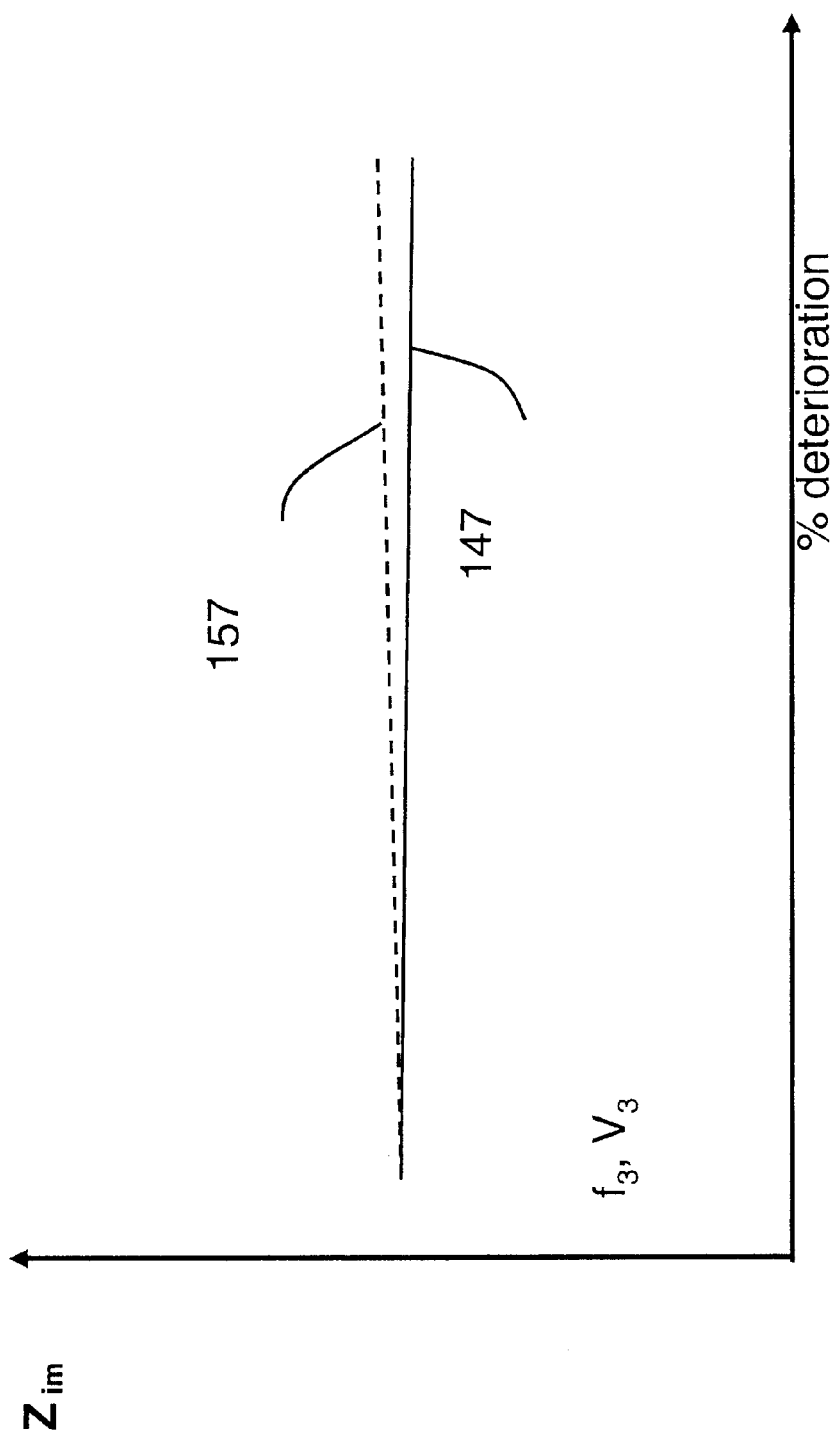

For many highly electrically-resistive fluids, catastrophic failure (e.g., water contamination) is readily detected in a particular frequency range and/or at particular DC offset voltages, while long term fluid degradation (e.g., oxidation or additive depletion) may be detected in other frequency ranges and/or at other DC offset voltages. Hence, to improve the response time in each instance, monitoring frequencies and DC offset voltages where catastrophic failure is readily detected separately from frequencies and DC offset voltages where longer-term fluid changes are readily detected may be desired. In this case, the embodiment of FIG. 6 is advantageous. In accordance with aspects of the present invention, FIG. 6 shows a fluid monitoring apparatus with two independently operated electrochemical monitoring systems A and B existing simultaneously in parallel. Note, the elements in respective systems A and B are labeled with their corresponding alpha-character in the reference numerals of FIG. 6, and similar numerically labeled elements in FIG. 6 correspond to and operate in essentially the same manner as their counterparts in FIG. 1. Note that while the embodiment shown in FIG. 6 has only two parallel systems, alternate embodiments can optionally include additional parallel systems.

In another embodiment, systems A and B are separately operated (essentially as described above) in parallel at different frequency ranges and/or different DC offset ranges suited to the ready detection or analysis of desired qualities and/or conditions of the fluid 5. For example, system A is optionally operated at the appropriate frequency range and DC offset range which provides for ready detection or detailed analysis related to catastrophic fluid failure, while system B is operated at the appropriate frequency range and DC offset range which provides for ready detection or detailed analysis related to relatively long-term fluid degradation or deterioration.

The embodiments described above employ signal generators that are capable of producing AC voltage at a continuous range of frequencies, which are optionally used to produce electrochemical impedance plots of the type shown in FIGS. 2, 3 and 4. Additionally, some of the signal generators (e.g., those of FIGS. 1 and 6) are also capable of producing AC voltages with a continuous range of DC offset voltages. Alternatively, however, the signal generators may only produce a determined number of discreet frequencies and/or a determined number of discreet DC offset voltages as desired for particular applications.

With reference to FIGS. 7(A)-7(F), graphs illustrate changes in $Z_{real}$ and $Z_{im}$ as a function of percent deterioration or degradation for a particular highly electrically-resistive fluid. Shown are plots for three discrete pairs of frequency/DC-offset-voltages, namely, $(f/V)_1$, $(f/V)_2$ and $(f/V)_3$. Curves 140, 141 are $Z_{real}$ and $Z_{im}$ respectively for oxidation degradation and curves 150. 151 are $Z_{real}$ and $Z_{im}$ respectively for contamination degradation at frequency/DC-offset-voltage $(f/V)_1$. Curves 143, 144 are $Z_{real}$ and $Z_{im}$ respectively for oxidation degradation and curves 153, 154 are $Z_{real}$ and $Z_{im}$ respectively for contamination degradation at frequency/DC-offset-voltage $(f/V)_2$. Curves 146, 147 are $Z_{real}$ and $Z_{im}$ respectively for oxidation degradation and curves 156, 157 are $Z_{real}$ and $Z_{im}$ respectively for contamination degradation at frequency/DC-offset-voltage $(f/V)_3$. In these FIGURES, the electrochemical impedance changes are linear functions of deterioration; that is, the curves are straight lines that vary as a function of either $P_o$ or $P_c$, where $P_o$ is percent deterioration due to oxidation and $P_c$ is percent deterioration due to contamination. If the fluid were to degrade only due to oxidation, the fluid condition could simply be determined from any one of curves 140, 141, 143, 144, 146 or 147. Similarly, if the fluid were to degrade only due to contamination, the fluid condition could simply be determined from any one of curves 150, 151, 153, 156 or 157. Typically, however, fluids degrade by multiple modes, and in this example the fluid degradation expected during normal use is due to both oxidation and contamination. If the fluid's electrochemical impedance change due to combined oxidation and contamination deterioration is a sum of deterioration due to each mode independently, the total change in $Z_{real}$ and $Z_{im}$ for any frequency/offset-voltage shown would be less than the change that occurs for each mode separately. Hence, multiple degradation modes confound a fluid condition analysis based on only one of the plots shown in FIGS. 7(A)-7(F). Nevertheless, when any two of the plots shown in FIGS. 7(A)-7(F) are chosen where the slopes of impedance change as a function of oxidation and contamination deterioration are independent, an algorithm may be used to solve simultaneous equations for unique values of $P_o$ and $P_c$, thereby determining the fluid condition.

In general, the slopes of the $Z_{real}$ and $Z_{im}$ curves are not independent for a given frequency and DC offset voltage; hence, more than one frequency/DC-offset-voltage is desirable if one wishes to arrive at the unique solution. Therefore, in the case where two deterioration or degradation modes exist, determining the electrochemical impedance of the fluid at two appropriate points with different frequency/DC-offset-voltages is highly advantageous. If additional (i.e., more than two) degradation modes are possible that affect the electrochemical impedance in a confounding manner, then determining the electrochemical impedance at an even greater number of appropriate points with distinct frequency/DC-offset-voltage is desirable to provide an appropriate analysis of the fluid's condition.

Note that while FIGS. 7(A)-7(F) show linear curves and the discussion above is for a case where impedance changes due to deterioration or degradation modes is additive, the same arguments hold for highly electrically-resistive fluids with non-linear deterioration curves and where the electrochemical impedance of multiple modes is not simply additive. Further note, the discussion of fluid condition based on the discrete curves of FIGS. 7(A)-7(F), or even the continuous curves of FIGS 2, 3 and 4 is based on one sequence of collected data. However, changes of fluid condition between sequences of data is also optionally used to analyze an unacceptable fluid condition. As an example, a sequence of electrochemical impedance data might show that the percent water contamination of a hydrocarbon fluid is within acceptable limits. However, without knowing the percent water contamination of the previous determination, the controller cannot analyze if water contamination is increasing, decreasing or remaining the same. By knowing the water contamination history, the controller may analyze that a fluid condition problem exists before the percent water exceeds acceptable limits.

Figure 8:
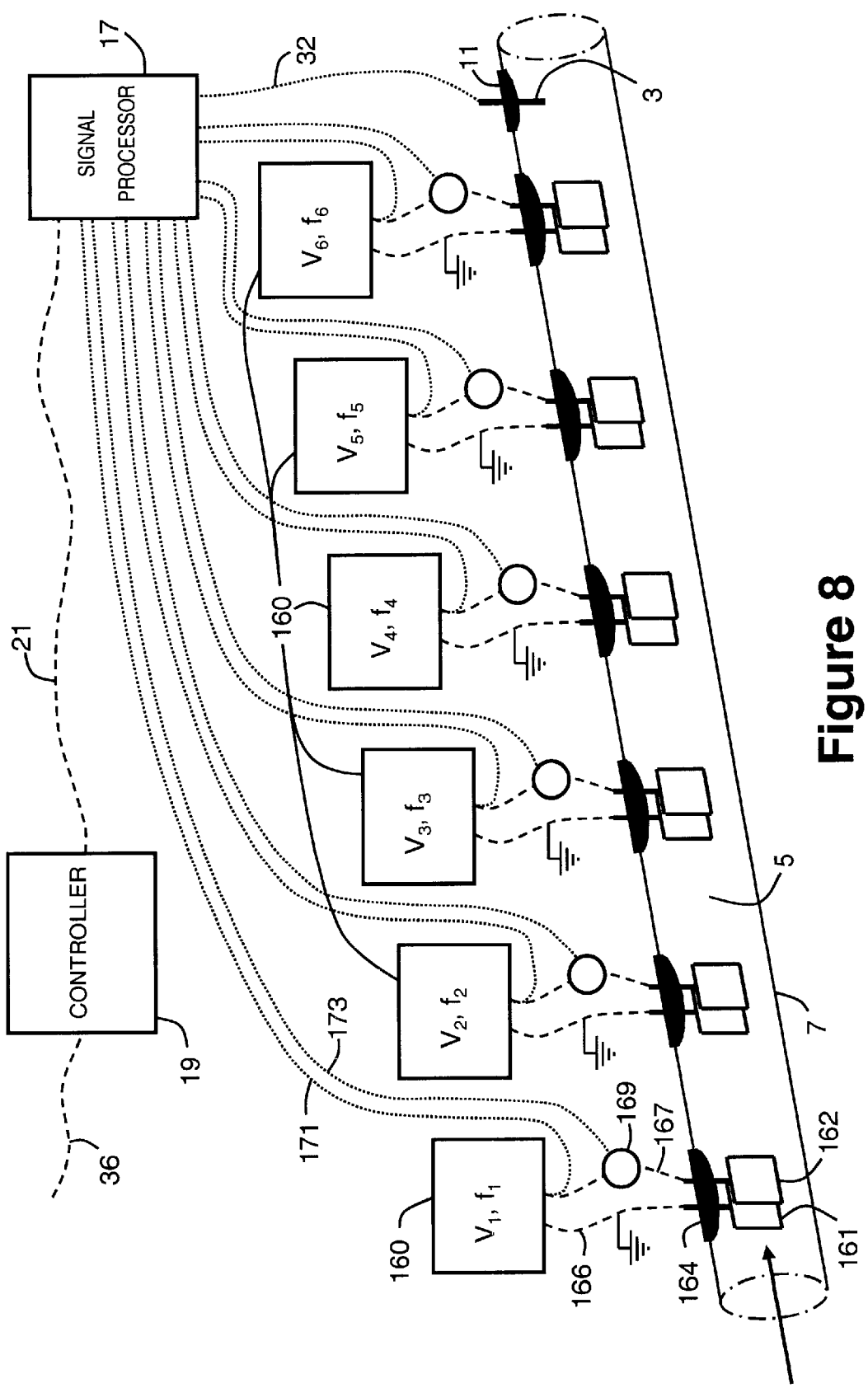
FIG. 8 is a schematic illustration showing another embodiment of an on-line fluid monitoring apparatus in accordance with aspects of the present invention.

With reference to FIG. 8, another exemplary embodiment of the fluid monitoring apparatus is shown with a plurality of parallel independently operated electrochemical monitoring-systems A through F. Note that while the exemplary embodiment shown in FIG. 8 has six parallel systems, alternate embodiments can optionally include a greater or lesser number of parallel systems. Preferably, the number of parallel systems use in a particular application is dependent on the composition of fluid 5, and on total number of deterioration or failure modes of fluid 5 that are of interest.

In any event, the elements in the respective systems A through F are labeled with their corresponding alpha-character in the reference numerals of FIG. 8, and similar numerically labeled elements in FIG. 8 correspond to and operate in essentially the same manner as their counterparts in FIG. 1. However, signal generators 13A through 13F each provide a distinct electrical output including a fixed frequency/DC-offset-voltage. As shown, the fixed frequency/DC-offset-voltage for generators 13A through 13F are $(f/V)_A$, $(f/V)_B$, $(f/V)_C$, $(f/V)_D$, $(f/V)_E$ and $(f/V)_F$, respectively. Another distinction from the embodiment of FIG. 1, is that controller 19 in this embodiment does not control the output of signal generators 13A through 13F since they each produce only one frequency/DC-offset-voltage. The FIG. 8 embodiment advantageously obtains a plurality of parallel electrochemical measurements of fluid 5 simultaneously with the measurements being at distinct fixed frequency/DC offset voltages.

Figure 9:
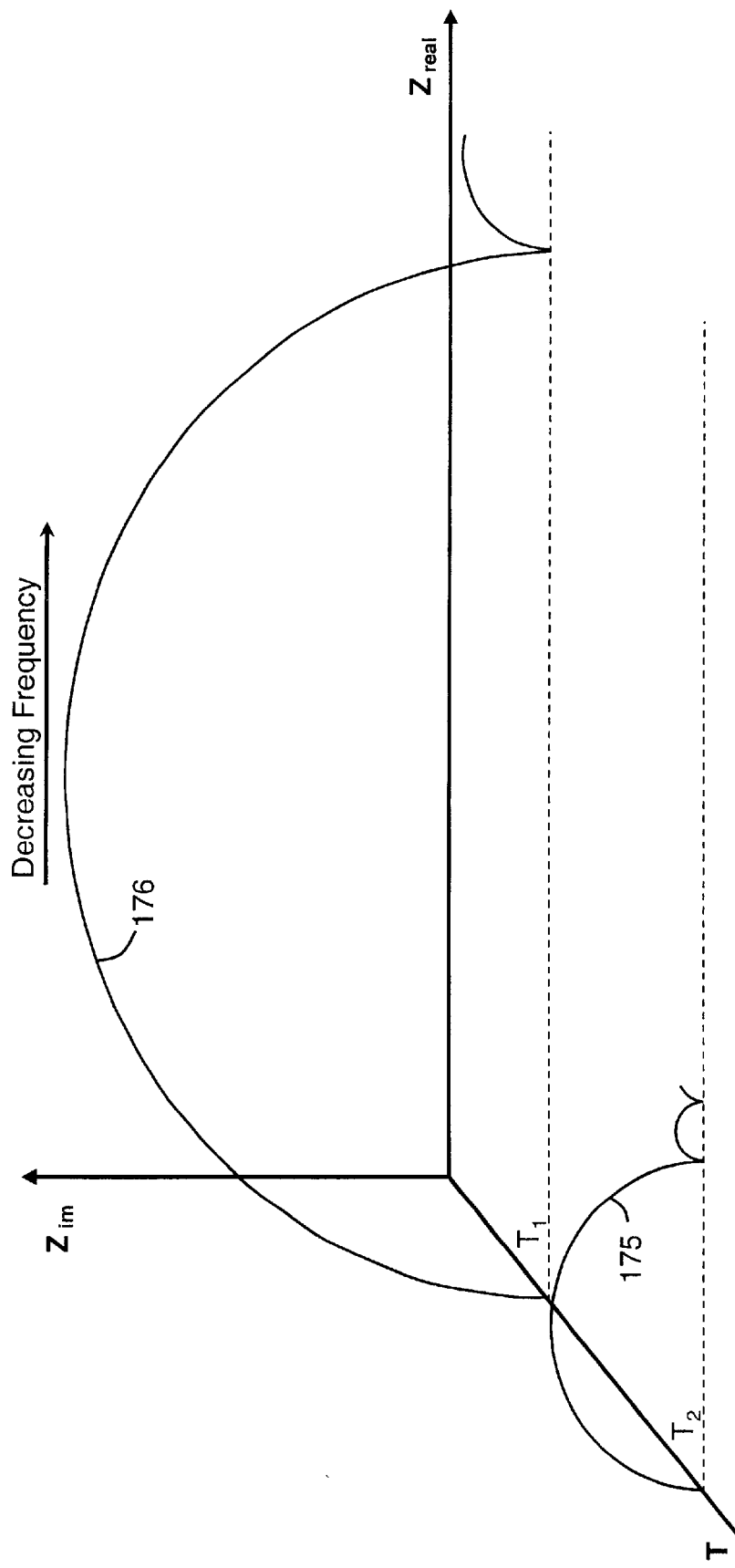
FIG. 9 is a representative graph illustrating the temperature dependence of a highly electrically-resistive fluid's electrochemical impedance.

The electrochemical impedance of a highly electrically-resistive fluid varies as a function of the fluid's temperature. FIG. 9 is a graph showing the electrochemical impedance of a highly electrically-resistive fluid taken at a DC offset voltage $V_o$ and temperatures $T_1$ and $T_2$, where $T_1$ is greater than $T_2$. Curve 175 at $T_1$ and curve 176 at $T_2$ where both generated using the same frequency range. While either analytical or empirical data is optionally used to temperature correct the data of curve 176 to the first portion of curve 175, curve 175 contains information about the fluid that is not contained in curve 176, e.g., note the complete smaller semi-circular portion of curve 175 which is incomplete in the curve 176. Nevertheless, by using lower frequencies (i.e., lower than those used to test the fluid at temperature $T_1$) to test the fluid at lower temperature $T_2$, the same level of detail and/or information regarding the fluid is obtainable. Lower frequencies, however, require significantly longer data collection times, thereby negatively impacting the response time of a fluid quality and/or condition determination.

Hence, in accordance with a preferred embodiment of the present invention, the fluid's temperature is optionally regulated via heating to optimize the response time. Preferably, the temperature regulation is carried out within the constraints of available power, packaging, and possible fluid degradation. Fluid heating is particularly desirable in applications where the fluid experiences a wide range of temperatures under normal operation. For example, in an "intermittent service" engine, oil temperature frequently varies between ambient and an ultimate operating temperature. As another example, the temperature of a metal working fluid often varies as a function of the hourly throughput and tool condition of the metal working equipment. Regulating fluid temperature while monitoring the fluid is also of particular benefit for the embodiment shown in FIG. 8 where temperature compensation of fixed frequency/DC-offset-voltage data may be more difficult if the fluid's temperature range is relatively large.

Figure 10:
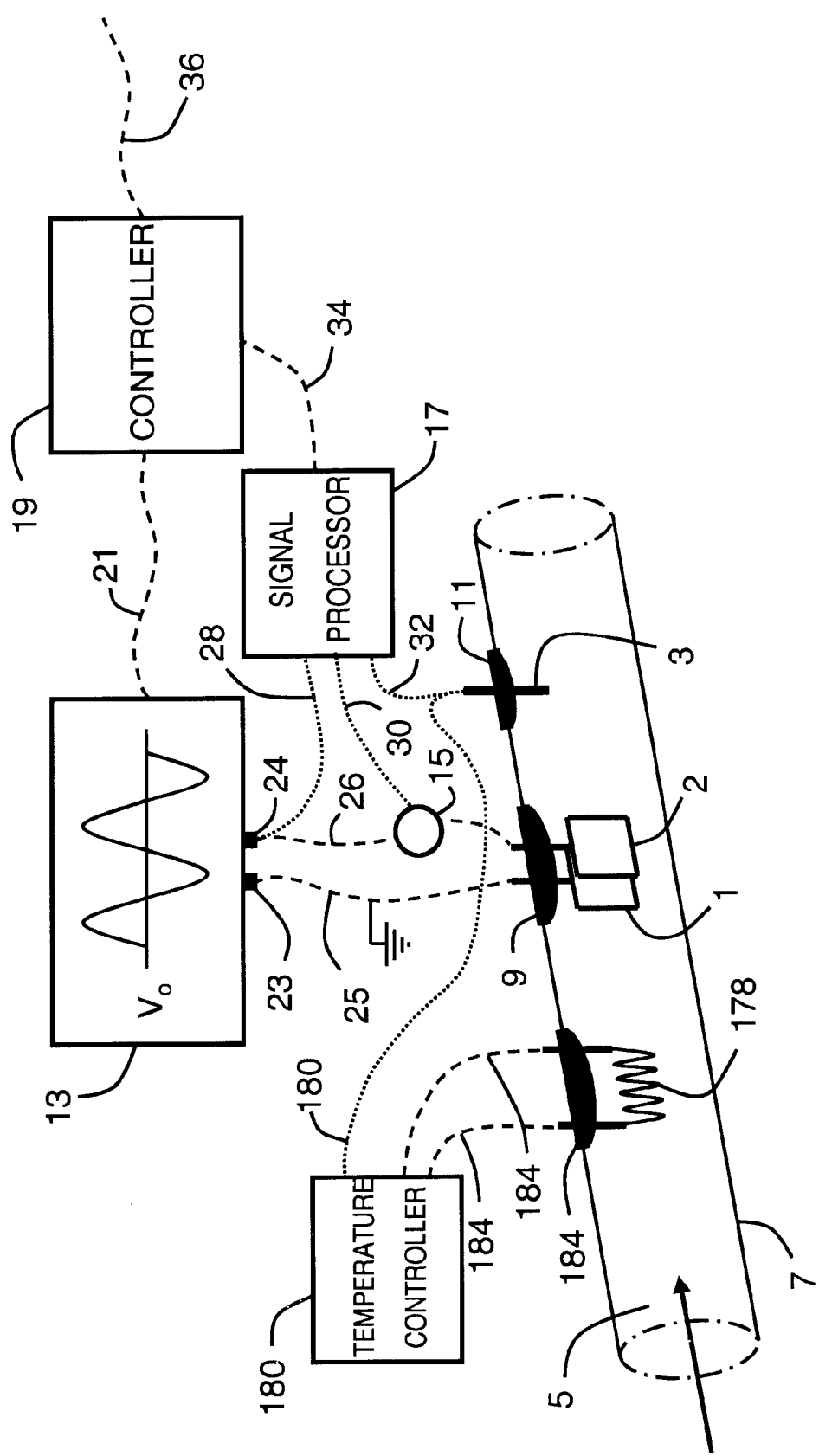
FIG. 10 is a schematic illustration showing another embodiment of an on-line fluid monitoring apparatus in accordance with aspects of the present invention.
Figure 11A:
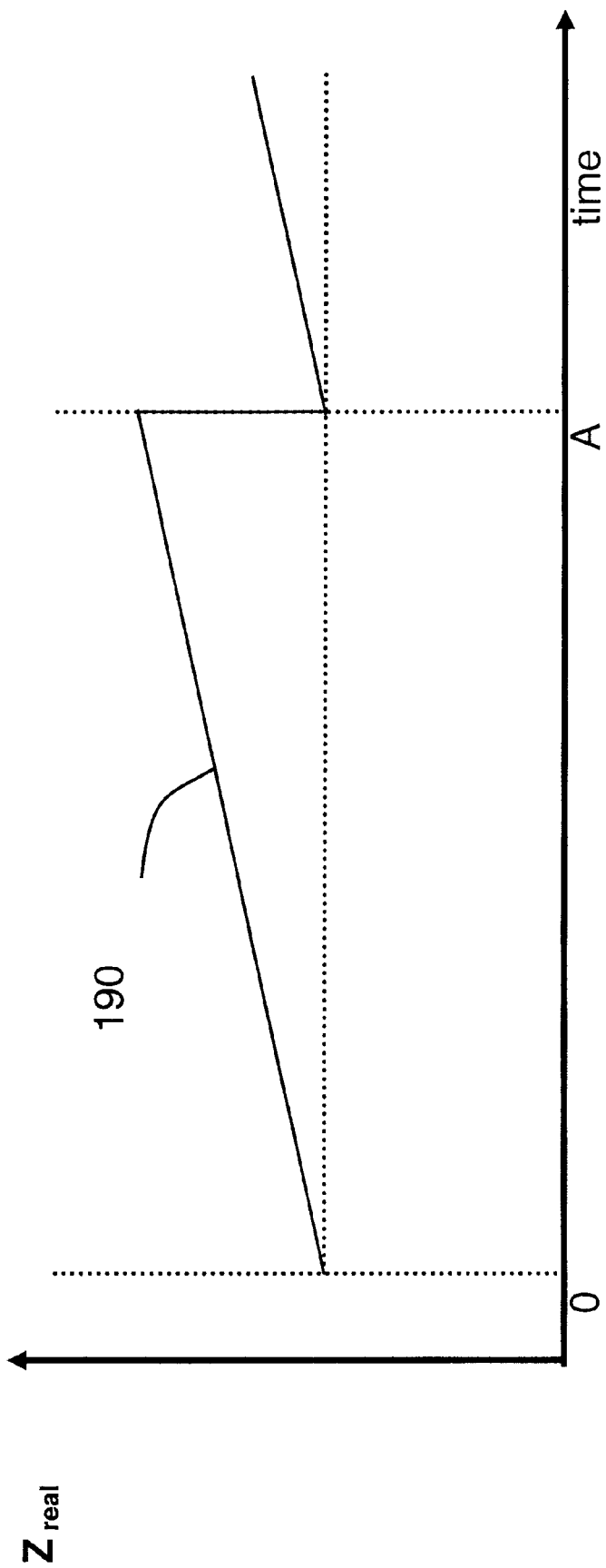
FIGS. 11(A)-11(D) include representative graphs illustrating the effect of a total fluid replacement on a fluid's electrochemical impedance.
Figure 11B:
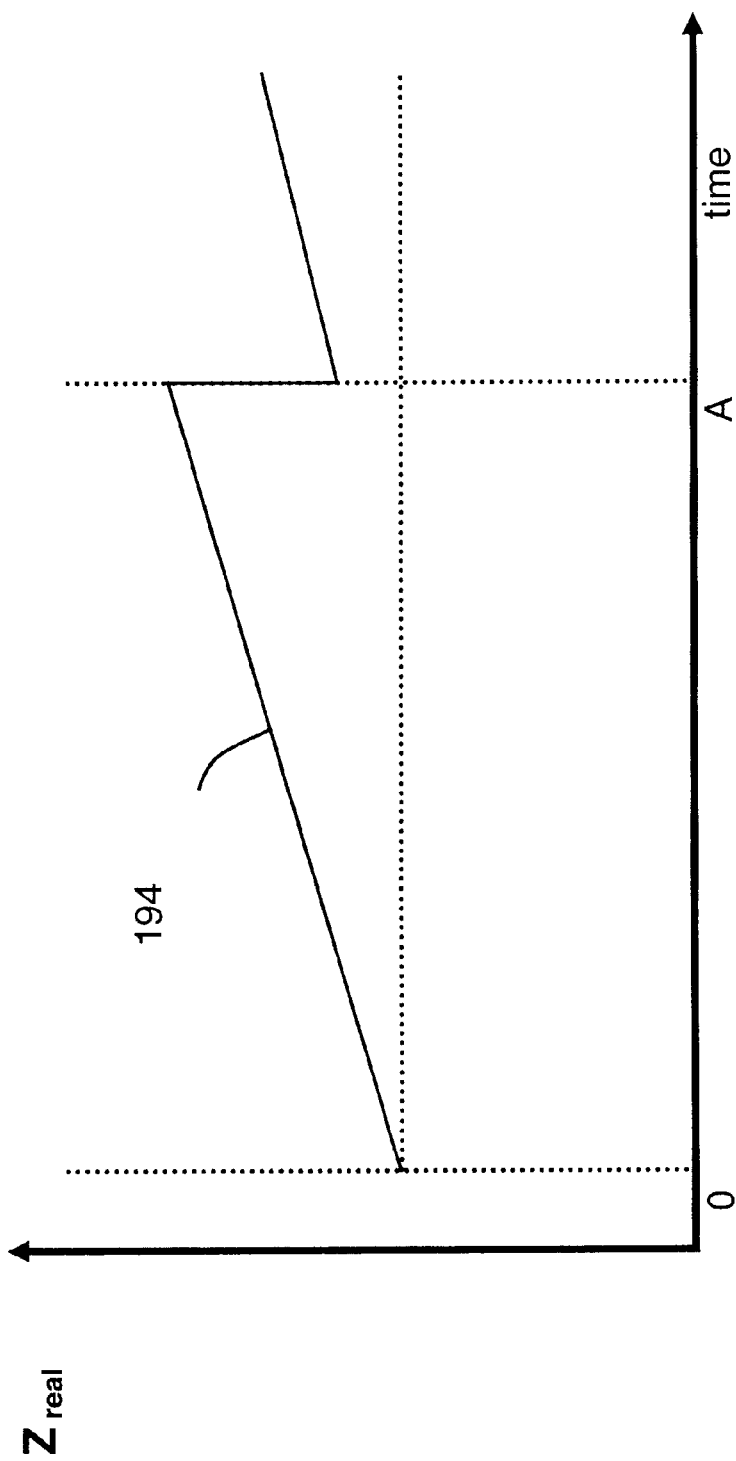
Figure 11C:
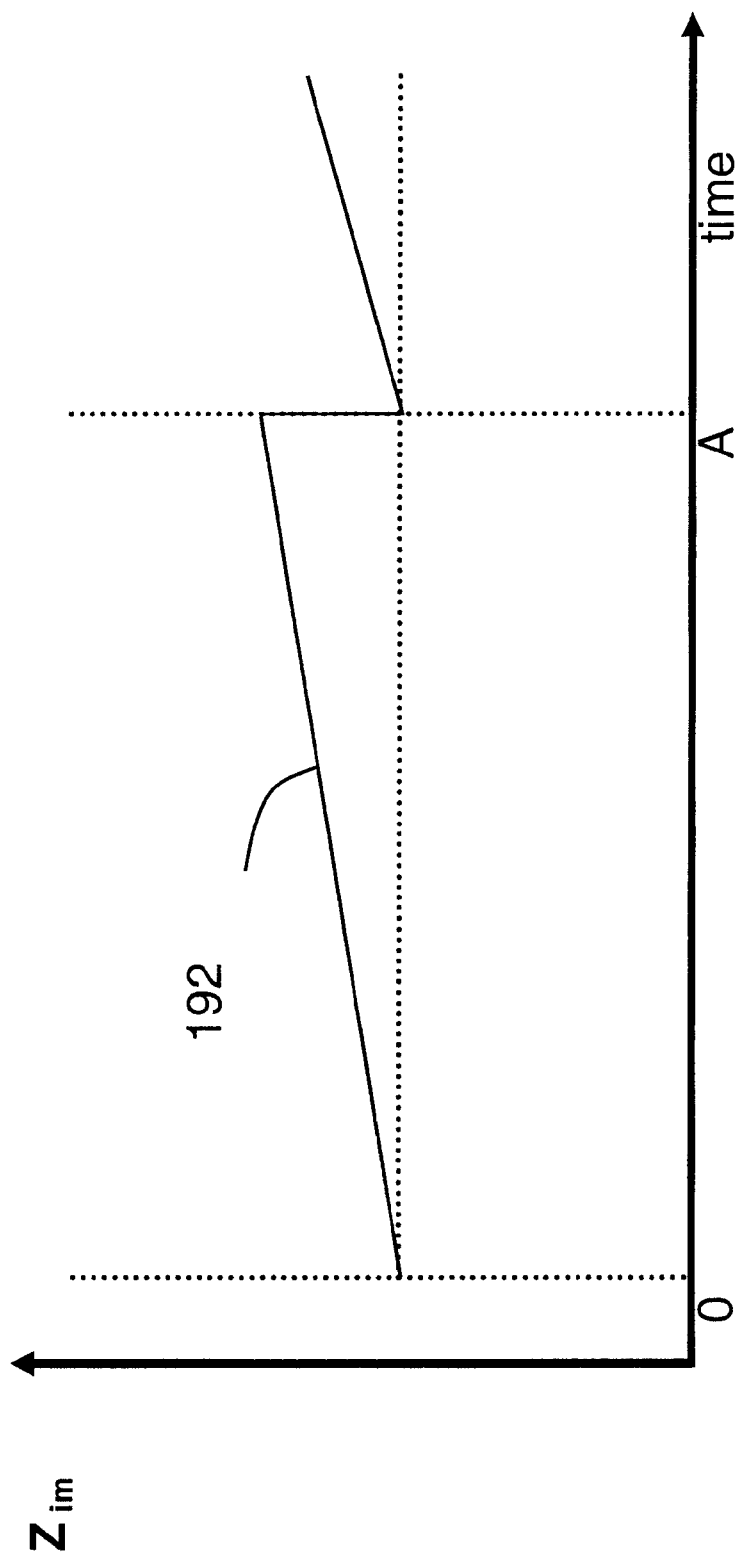
Figure 11D:
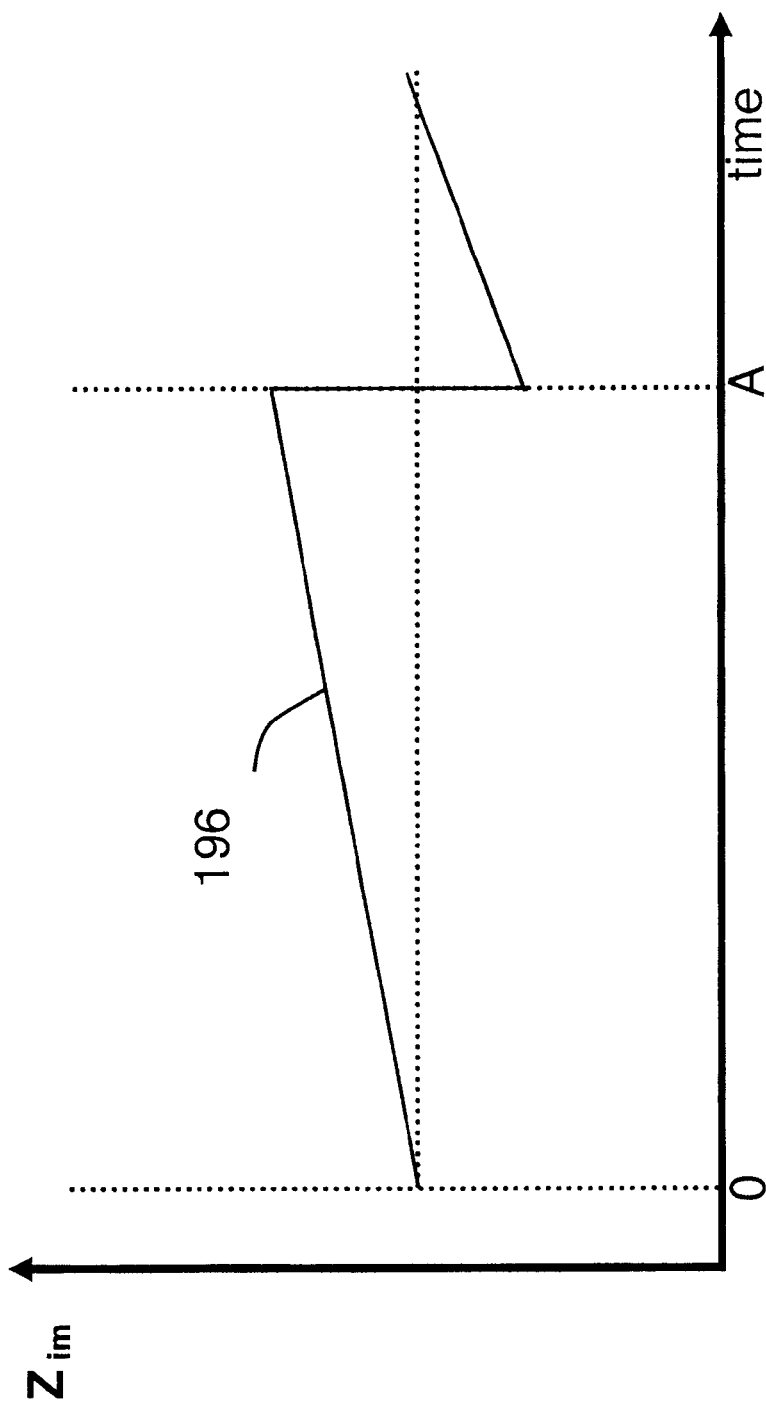

With reference to FIG. 10, an exemplary embodiment of the fluid monitoring apparatus is shown which incorporates a temperature regulation feature in accordance with aspects of the present invention. In particular, FIG. 10 shows the fluid monitoring apparatus of FIG. 1 with an additional system or apparatus for temperature regulation of fluid 5. As shown, the temperature regulation system includes a heater 178 and temperature controller 180 for controlling the temperature of fluid 5. Heater 178 is immersed in fluid 5 and is fixedly held in conduit 7 with mount 182. Temperature controller 180 monitors thermocouple 3 via electrical conduit 184, and selectively applies electrical power to heater 178 through electrical conduits 186, 188 to achieve and maintain the fluid's temperature at a desired level.

Optionally, when fluid 5 is not at the designated control temperature, e.g. at the start of fluid monitoring, controller 19 is programmed to temperature compensate data from signal processor 17 to analyze fluid quality and/or condition, or controller 19 may be programmed to not analyze fluid quality and/or condition until the designated control temperature is reached. If fluid 5, as sensed by thermocouple 3, is not at control temperature, controller 19 is optionally programmed to output information to that effect. In addition, if the temperature of fluid 5 is not achieving the designated control temperature, controller 19 is optionally programmed to output information that the monitoring apparatus is not functioning properly.

Although not shown in FIG. 10, an alternate embodiment optionally has temperature controller 180 controlled by controller 19 through an electrical conduit. In this alternate embodiment, controller 19 determines and sets the designated control temperature for temperature controller 180 based on inputs from signal processor 17 or other relevant inputs.

Note that while shown apart from one another for illustrative purposes in FIG. 10, the location of the heater, electrodes and/or temperature sensor relative to one another is selected to achieve proximity advantageous for the particular application. For example, if the apparatus is compactly packaged with relatively small electrode separation, fluid heating is optionally accomplished by heating electrodes 1, 2 and monitoring the fluid temperature either between or in the immediate vicinity of the electrodes.

While the descriptions above afford continuous fluid monitoring in an on-line environment, recognizing when fresh fluid is added to the system can be advantageous when monitoring fluid quality and/or condition. There are essentially two types of fluid refreshment, namely, substantial or total fluid replacement (e.g., a complete oil change) and intermittent refreshment (e.g., refueling). In accordance with aspects of the present invention, fresh fluid recognition suitable to either one or both types of refreshment is an incorporated feature of the fluid monitoring apparatus or device.

With reference to FIGS. 11(A)-11(D), graphs show a highly electrically-resistive fluid's $Z_{real}$ and $Z_{im}$ at a particular frequency and DC offset voltage as a function of time where a complete fluid change is made at time "A". Curves 190, 192 are $Z_{real}$ and $Z_{im}$ respectively for a case of a "closed" fluid system, i.e., a system where the fluid is not consumed or loss during use, where the fluid is replaced with a fresh fluid of the same quality. At time "A", curves 190, 192 return to the time equal 0 values, which is when the replaced fluid was fresh. Curves 194, 196 are $Z_{real}$ and $Z_{im}$ respectively for a case where the fluid is replaced with a fresh fluid that is of a different quality. At time "A", 194, 196 do not return to the time equal 0 values.

For applications where only complete fluid replacements occur, one technique that can be selected for identifying a fluid change is to program controller 19 to interpret either certain types or all abrupt and significant electrochemical impedance changes as a fluid change. In this technique, when controller 19 determines that a fluid change has occurred, controller 19 uses the next sequence of electrochemical impedance data to analyze and communicate information about the fluid quality. Another method of identifying a fluid change is for controller 19 to include an input for receiving conclusive information from outside the fluid monitoring apparatus that a fluid change has occurred, e.g., the service technician may manually indicate or enter data into controller 19 or may reset controller 19 when the fluid is changed.

Figure 12:
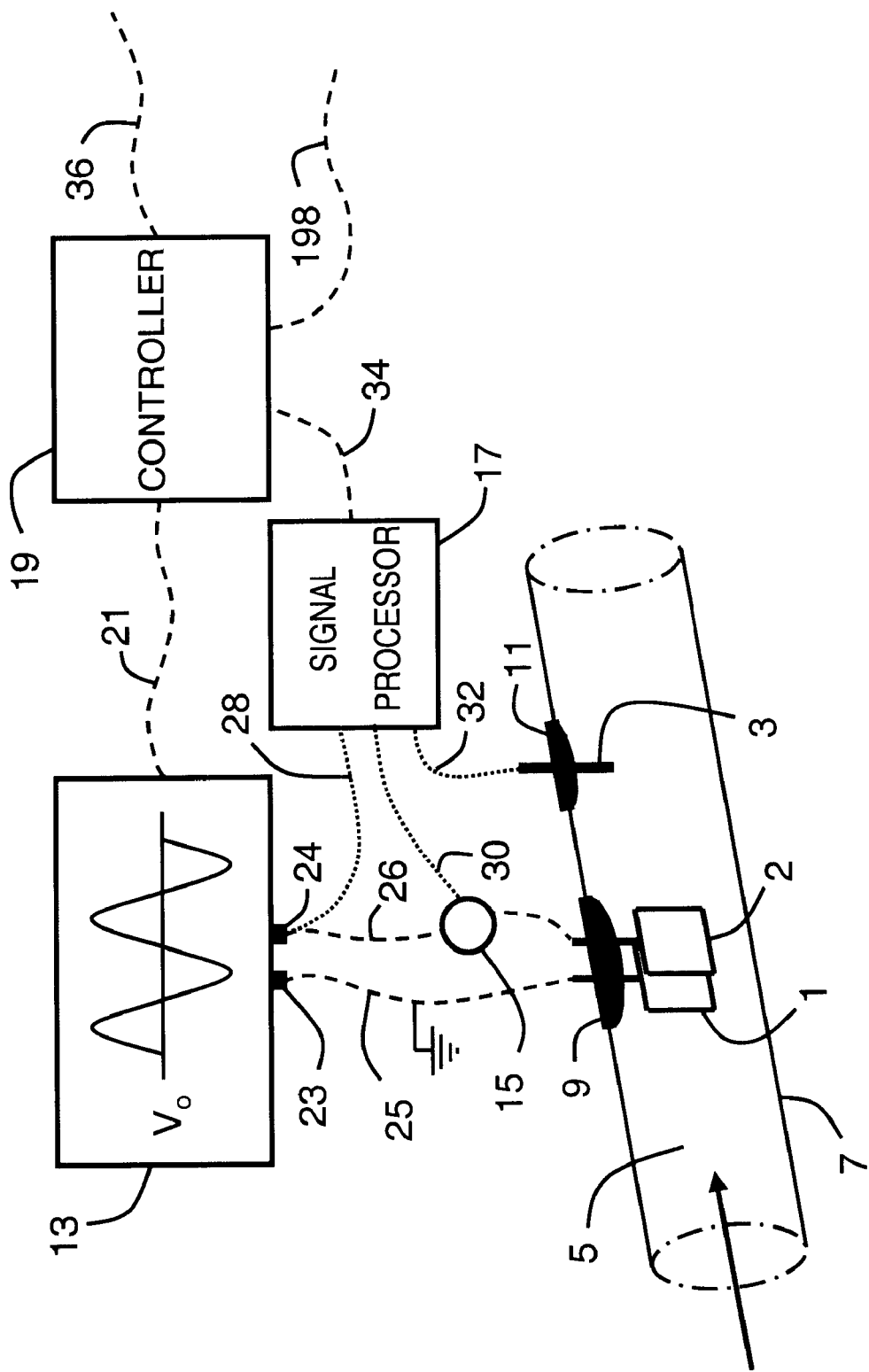
FIG. 12 includes schematic illustrations illustrating the effect of partial fresh fluid additions on a fluid's electrochemical impedance.
Figure 13A:
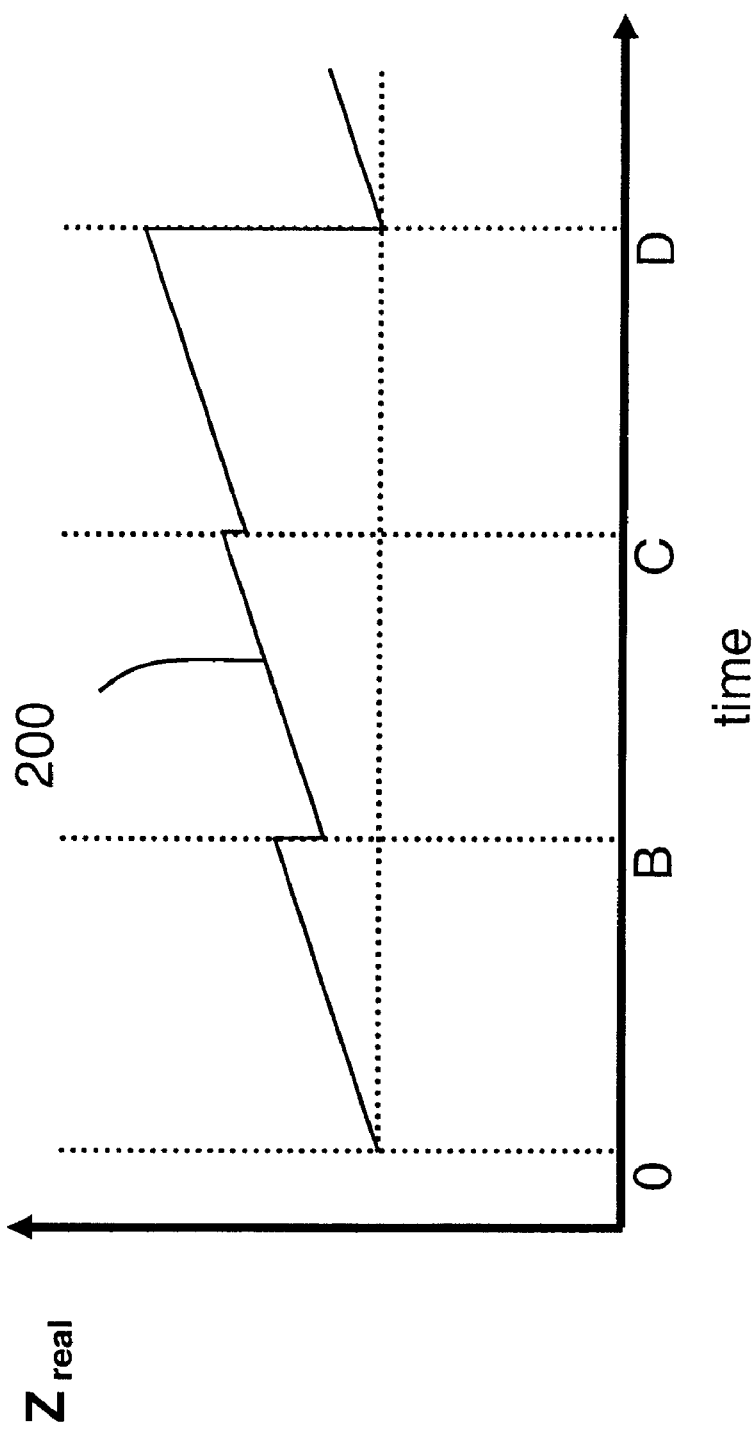
FIGS. 13(A) and 13(B) are representative graphs showing another embodiment of an on-line fluid monitoring apparatus in accordance with aspects of the present invention.
Figure 13B:
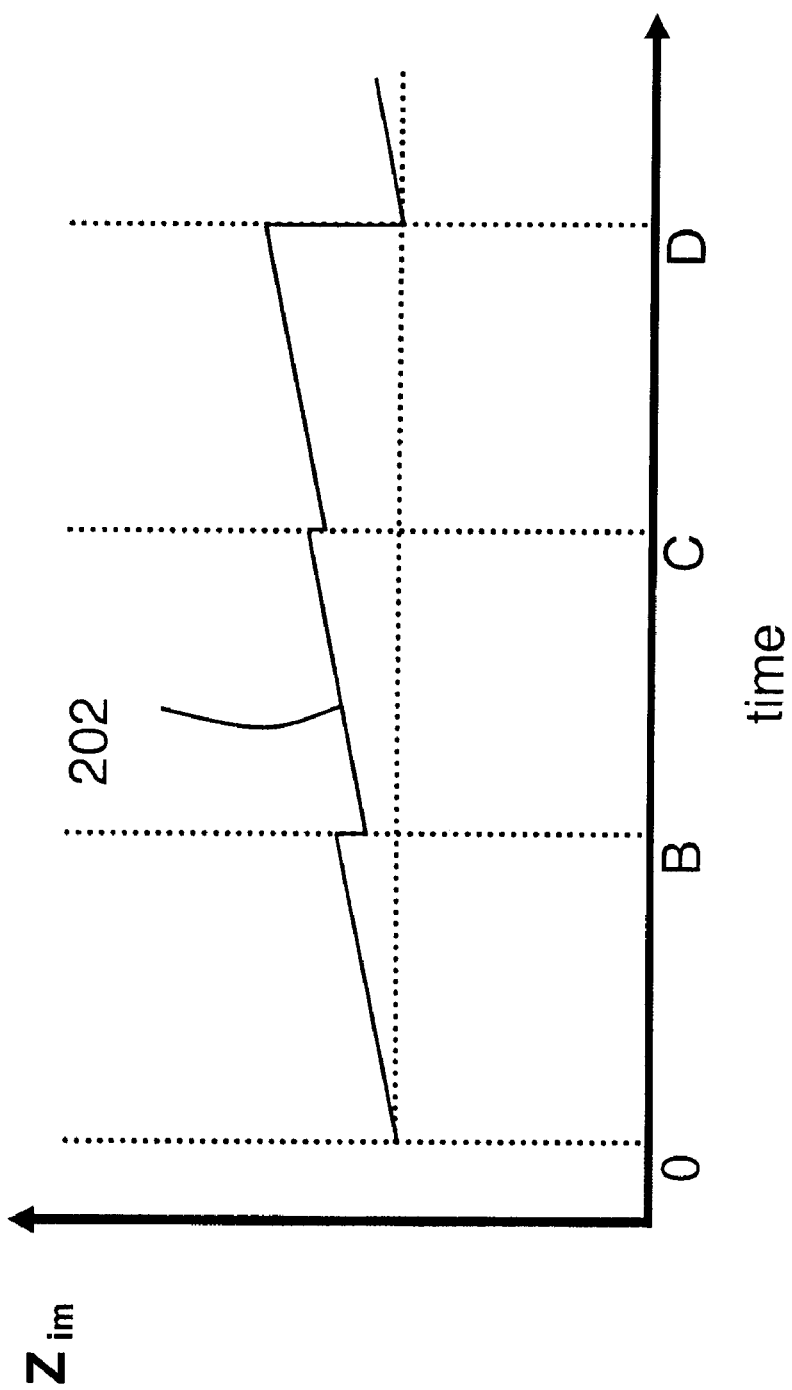

While the above methods work well for applications where only total fluid replacement occurs; many applications perform fresh fluid additions without all of the previous fluid being removed, so called, intermittent refreshment. For examples, certain applications provide for partial fresh fluid additions to replace consumed or lost fluid during operation, and other applications maintain fluid quality during use by partial exchanges of fresh fluid for used fluid. FIG. 12 shows graphs of a fluid's $Z_{real}$ and $Z_{im}$ at a particular frequency/DC-offset-voltage as a function of time for a case of an "essentially closed" system, i.e. a system where some fluid consumption or loss can occur, where two partial additions of fresh fluid are made at times "B" and "C" and a complete fluid replacement is made at time "D". Curves 200, 202 are $Z_{real}$ and $Z_{im}$ respectively. Interpreting the data at times "B" and "C" is problematic without knowing the concentration of fresh fluid added (i.e. percentage of the fresh fluid to the total fluid volume). Without fresh fluid concentration data, the larger change in curves 200, 202 at time "B" than at time "C" may be due to a larger percentage of fresh fluid being added, a different quality of the fresh fluid being added, or both.

In a preferred embodiment, the highly-electrically-resistive-fluid monitoring apparatus obtains information about the fresh fluid concentration to allow fresh fluid quality to be uniquely determined in applications where partial fluid replacement is selectively being made. Concentration information is optionally obtained from an independent external source, e.g., via an input to controller 19. That is, in addition to information that a fresh fluid addition is being made, fresh fluid concentration information or information that allows a determination of the fresh fluid concentration may also be input. In operation, controller 19 uses the input information and the next sequence of data from signal processor 17 to make a fluid quality analysis and to communicate information about fluid quality through communication conduit 36.

In an alternate embodiment, input information about a complete or partial fresh fluid addition does not come from an external source. With reference to FIG. 12, the fluid monitoring apparatus of FIG. 1 is shown with an additional system for monitoring fresh fluid additions (complete or partial), thereby providing for fluid quality analyses to be made without external input.

As shown in FIG. 12, fluid 5 is contained in a fluid circuit of a device or system (not shown), which includes conduit 7 and fluid reservoir 205. In normal device or system operation, fluid 5 circulates from reservoir 205, through the fluid circuit including conduit 7, to where the fluid is used or consumed. In many applications, either all or a portion of fluid 5 is returned to reservoir 205 after circulating through conduit 7.

Signal processor 17 monitors a level sensor 210 through electrical conduit 212. Signal processor 17 converts the monitored inputs into suitable signals that are input to controller 19 through electrical conduit 34. Preferably, signal processor 17 continuously monitors level 207 of fluid 5 using level sensor 210 and electrical conduit 212, and communicates level information to controller 19 that is programmed to use the level information to determine the concentration of fresh fluid additions. Each time a fresh fluid addition is determined, controller 19 is programmed to use the determined fresh fluid concentration, and voltage, current and temperature information from signal processor 17, to analyze the quality of the added fresh fluid and the condition of the total volume of fluid 5. Controller 19, using communication conduit 36, outputs the analyzed quality and condition information that, for example, is optionally used to alert an operator or service technician if an improper quality fluid is added to reservoir 205 or if the condition of fluid 5 is not within acceptable limits. Alternately, the analyzed quality and/or condition information is optionally used by a higher level system (not shown) that maintains the condition of fluid 5 or that controls a device or system using fluid 5.

While electrodes 1, 2 and thermocouple 3 are shown in FIG. 12 as mounted in conduit 7, optionally, they are similarly mounted in fluid reservoir 205 where they are immersed at a point where adequate mixing of fluid 5 occurs. This is advantage insomuch as, when so mounted, the fluid monitoring apparatus may be package together into a single module including the level sensor.

Preferably, the embodiment of FIG. 12 is used for applications where removal, consumption or loss of used fluid 5 is not simultaneous with the addition of fresh fluid, or where fluid removal, consumption or loss is predictable and programmed into the algorithm of controller 19. Optionally, devices other than a level sensor are used to determine the concentration of fresh fluid additions to reservoir 205. For example, a fluid flow meter or flow meters in conduits used to fill or drain fluid reservoir 205 are used in place of or in addition to level meter 210 in fluid reservoir 205 to determine fresh fluid additions and/or concentrations.

EXAMPLE

To demonstrate the techniques of the present invention, the electrochemical impedance of an engine oil, which had an initial 20° C. bulk-resistivity of about $10^8$ ohm-m, was measured for a series of samples removed at fixed intervals from an operating gasoline internal combustion engine. Measurements were made using two 1 cm$^2$ parallel plate platinum electrodes, with 0.5 mm electrode separation, immersed in the flowing fluid. Measurements were made at fixed temperatures over the range of about 40° C. to about 120° C. in about 10° C. increments. A Voltalab40® electrochemical workstation with Radiometer® Inc. software was used to provide the signal to the electrodes and to calculate the electrochemical impedance. The peak AC voltage amplitude was about ±0.5 V. A frequency range from about 10° MHz to about 10° mHz was employed using about 116 frequencies that required about 50 minutes to collect data over the range. The DC offset voltages used were about 0, about 3, about 6, about 9, about 12 and about 14 V. The data obtained in this example were consistent with the electrochemical impedance data shown in FIGS. 2 and 3. The zero DC offset voltage electrochemical impedance curves show relatively little change as the engine oil deteriorated due to use. The non-zero DC offset voltage electrochemical impedance curves showed significantly more detail of the oil degradation due to use.

While the invention has been described with reference to the preferred embodiments, obviously, modifications and alterations will occur to others upon reading and understanding the proceeding detailed description. The intent is that the invention be construed as including all such modifications and alterations insofar as they come within the scope of the appended claims or the equivalents thereof.

What is claimed:

1. A method of monitoring a highly electrically-resistive fluid comprising:
   a) applying an AC electrical potential across the fluid at a first frequency and a first DC offset such that a first electrical response results;
   b) measuring the resulting first electrical response;
   c) applying the AC electrical potential across the fluid at a second frequency for a non-zero first DC offset voltage, a second DC offset or combinations thereof resulting in a second electrical response; wherein the second frequency and the second DC offset being different from the first frequency and the first DC offset respectively;
   d) measuring the resulting second electrical response; and
   e) analyzing the fluid's quality and/or condition from the measured first and second electrical responses to the respective first and second applied electrical potentials.

2. The method of claim 1 wherein the fluid is selected from the group consisting of lubricants, natural and/or synthetic motor oils, standard additives and/or adjuncts, combustion engine fuels, other hydrocarbon-based fluids used in transportation and industrial applications, and combinations thereof.

3. The method of claim 1 comprising:
   a) repeatedly applying the AC potentials;
   b) repeatedly measuring the resulting electrical responses; and
   c) analyzing the fluid's quality and/or condition from the measured first and second electrical responses and/or changes in the measured first and second electrical responses to the respective first and second applied electrical potentials.

4. The method of claim 3 comprising controlling the applied AC potentials based on determined electrical impedance, analyzed fluid quality condition and combinations thereof.

5. The method of claim 1 comprising measuring the fluid's temperature.

6. The method of claim 5 comprising compensating the fluid quality and/or condition analysis for variations in fluid temperature.

7. The method of claim 5 comprising controlling the applied AC potentials based on measured temperature.

8. The method of claim 5 comprising heating the fluid being monitored to a desired temperature.

9. The method of claim 1 comprising determining the quality of a refreshment fluid when either a complete replacement or a partial refreshment of the monitored fluid occurs.

10. The method of claim 1 wherein the first and second electrical responses are currents resulting from the applied AC electrical potentials.

11. The method of claim 1 wherein the fluid quality and/or condition is analyzed using electrical impedance values determined from measured electrical responses corresponding to applied electrical potentials.

12. A method of monitoring a highly electrically-resistive fluid comprising the steps of:
   a) applying across a fluid an AC signal that includes at least two different AC electrical potentials with at least one AC electrical potential having a non-zero DC offset;
   b) measuring the fluid's electrical response at each applied potential; and
   c) analyzing the fluid's quality and/or condition using the applied AC signal and corresponding measured electrical responses.

13. The method of claim 12 wherein the fluid is selected from the group consisting of lubricants, natural and/or synthetic motor oils, standard additives and/or adjuncts, combustion engine fuels, other hydrocarbon-based fluids used in transportation and industrial applications, and combinations thereof.

14. The method of claim 13 comprising measuring the fluid's temperature variation in the fluid's temperature.

15. The method of claim 14 comprising controlling the applied AC potentials based on measured temperature.

16. The method of claim 14 comprising heating the fluid being monitored to a desired temperature.

17. The method of claim 12 comprising:
   a) repeatedly applying the AC signal;
   b) repeatedly measuring the resulting electrical responses; and
   c) analyzing the fluid's quality and/or condition using the applied AC signal and the measured corresponding electrical responses.

18. The method of claim 12 wherein the AC signal is an AC electrical potentials, the DC offset is held fixed, and the frequency is swept from one frequency to another by a method selected from a continuous manner, a series of discreet frequency steps for at least one non-zero DC offset or combinations thereof.

19. The method of claim 12 wherein the AC signal is an AC electrical potentials, the frequency is held fixed, and the DC offset voltage is swept from one DC offset voltage to another by a method selected from a continuous manner, a series of discreet voltage steps for at least one frequency, or combinations thereof.

20. The method of claim 12 comprising determining the quality of a refreshment fluid when either a complete replacement or a partial refreshment of the monitored fluid occurs.

21. The method of claim 12 wherein the first and second electrical responses are currents resulting from the applied AC electrical potentials.

22. The method of claim 12 wherein the fluid quality and/or condition is analyzed using electrical impedance values determined from measured electrical responses corresponding to applied electrical potentials.

23. An apparatus to monitor a highly electrically-resistive fluid comprising:
   a) at least a pair of separated electrodes that are immersed in a fluid being monitored;
   b) at least one signal generator that applies to the electrodes an electrical signal with at least two different AC potentials with at least one potential having a non-zero DC offset;
   c) at least one monitor that measures electrical response to the applied signal; and
   d) a controller that analyzes applied electrical signal and corresponding measured electrical response to determine the quality and/or condition of the fluid.

24. The apparatus of claim 23 wherein the electrical response monitor is a current sensor, which measures a current generated in response to the applied potentials.

25. The apparatus of claim 23 wherein the controller controls the signal generator.

26. The apparatus of claim 23 further includes a temperature sensor that monitors a temperature of the fluid.

27. The apparatus of claim 26 further includes a means to compensate the determined fluid quality and/or condition with the monitored temperature of the fluid.

28. The apparatus of claim 26 further includes a means for controlling the signal generator with the monitored temperature of the fluid.

29. The apparatus of claim 23 further includes a temperature control means for regulating the temperature of the fluid being monitored.

30. The apparatus of claim 23 further includes a means for the controller to determine when the fluid being monitored is totally replaced.

31. The apparatus of claim 23 further includes a means for the controller to determine when a fluid is partially refreshed and the concentration of the refreshment fluid.

32. The apparatus of claim 23 wherein the frequencies are selected from a group consisting of at least two different frequencies for a non-zero DC offset, the DC offsets are selected such that there are at least two different DC offsets, and combinations thereof.

33. An apparatus to monitor a highly electrically-resistive fluid comprising:
   a) a sensing means in contact with a fluid being monitored;
   b) a signal generator means in electrical communication with the sensing means, said signal generating means applying to the sensing means an electrical signal with at least two different AC potentials with at least one potential having a non-zero DC offset;
   c) a monitoring means that measures electrical response to the applied signal; and
   d) a control means that analyzes applied electrical signal and corresponding measured electrical response to determine the quality and/or condition of the fluid.

34. The apparatus of claim 33 wherein the control means controls the signal generator means.

35. The apparatus of claim 33 further includes a means the monitors a temperature of the fluid.

36. The apparatus of claim 35 further includes a means to compensate the determined fluid quality and/or condition with that monitored temperature of the fluid.

37. The apparatus of claim 35 further includes a means for controlling the signal generator means with the monitored fluid temperature.

38. The apparatus of claim 33 further includes a means for regulating the temperature of the fluid being monitored.

39. The apparatus of claim 33 further includes a means for the controller to determine when the fluid being monitored is totally replaced.

40. The apparatus of claim 33 further includes a means for the controller to determine when the fluid being monitored is partially refreshed and the concentration of the refreshment fluid.

* * * * *